(12) United States Patent
Rady et al.

(10) Patent No.: US 11,391,417 B2
(45) Date of Patent: *Jul. 19, 2022

(54) PIPELINE INTERCHANGE/TRANSMIX

(71) Applicant: PHILLIPS 66 COMPANY, Houston, TX (US)

(72) Inventors: Paul Rady, Katy, TX (US); Marisa Purificato, Cypress, TX (US); Franklin Uba, Bartlesville, OK (US); Ayuba Fasasi, Bartlesville, OK (US)

(73) Assignee: Phillips 66 Company, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/306,332

(22) Filed: May 3, 2021

(65) Prior Publication Data
US 2021/0254792 A1    Aug. 19, 2021

Related U.S. Application Data

(63) Continuation-in-part of application No. 16/391,817, filed on Apr. 23, 2019, now Pat. No. 11,022,986, and
(Continued)

(51) Int. Cl.
*F17D 3/01* (2006.01)
*G01N 33/28* (2006.01)
(Continued)

(52) U.S. Cl.
CPC ............. *F17D 3/01* (2013.01); *F17D 1/08* (2013.01); *F17D 3/05* (2013.01); *G01N 33/2829* (2013.01);
(Continued)

(58) Field of Classification Search
CPC .......... G01N 33/2821; G01N 33/2829; G01N 33/2835; G01J 3/42; G01J 3/44;
(Continued)

(56) References Cited

U.S. PATENT DOCUMENTS 2,859,757 A * 11/1958 Parsons .................. F16L 55/00
137/93
3,256,901 A *  6/1966 Kline, Jr. ............. B01J 19/0006
330/110
(Continued)

FOREIGN PATENT DOCUMENTS

| CA | 2055408 | 8/2020 |
| WO | 2017061994 A1 | 4/2017 |
| WO | 2019217067 | 4/2019 |

OTHER PUBLICATIONS

PCT Notification of Transmittal of the International Search Report and the Written Opinion of the International Searching Authority, or the Declaration, dated Jul. 2019, 12 pages.

*Primary Examiner* — William M McCalister
(74) *Attorney, Agent, or Firm* — Phillips 66 Company

(57) ABSTRACT

In one embodiment, a pipeline interchange is described where a first product flows through a first pipeline and a second product flows through a second pipeline. A pipeline interchange is connected downstream to both the first pipeline and the second pipeline, wherein the pipeline interchange blends the first product flowing through the first pipeline with the second product flowing through the second pipeline. A third pipeline is connected downstream to the pipeline interchange, wherein the third pipeline flows a blended product created from the blending of the first product and the second product in the pipeline interchange. An automated analyzer can be situated downstream of the pipeline interchange capable of physical and/or chemically analyzing the blended product and generating blended data. A data analyzer is also positioned to interpret the blended data and communicate adjustments to the flow of both the first product and the second product to achieve desired physical and/or chemical characteristics in the blended product.

9 Claims, 16 Drawing Sheets

Related U.S. Application Data a continuation-in-part of application No. 16/557,315, filed on Aug. 30, 2019, now abandoned.

(51) Int. Cl.
| | |
|---|---|
| *G05D 7/06* | (2006.01) |
| *F17D 3/05* | (2006.01) |
| *G05D 11/13* | (2006.01) |
| *G01J 3/44* | (2006.01) |
| *G01J 3/42* | (2006.01) |
| *F17D 1/08* | (2006.01) |

(52) U.S. Cl.
CPC .............. *G05D 7/0652* (2013.01); *G01J 3/42* (2013.01); *G01J 3/44* (2013.01); *G05B 2219/37371* (2013.01); *G05D 11/135* (2013.01); *G05D 11/139* (2013.01); *Y10T 137/2509* (2015.04); *Y10T 137/7736* (2015.04)

(58) Field of Classification Search
CPC .............. G05B 2219/37371; F17D 3/01; Y10T 137/2506; Y10T 137/2509; Y10T 137/7736; G05D 11/131; G05D 11/132; G05D 11/135; G05D 11/139; G05D 21/02
USPC .......................................... 137/92, 93, 467.5
See application file for complete search history.

(56) References Cited

U.S. PATENT DOCUMENTS

| | | | | |
|---|---|---|---|---|
| 3,256,902 | A * | 6/1966 | Porter | B01J 19/0006 700/265 |
| 3,451,402 | A * | 6/1969 | Howard | F02M 63/00 137/3 |
| 3,464,447 | A * | 9/1969 | Jones | F16K 11/22 137/883 |
| 3,530,867 | A * | 9/1970 | Hass | G01N 7/14 137/88 |
| 3,864,095 | A * | 2/1975 | Sinclair | G05D 21/02 137/3 |
| 3,999,959 | A * | 12/1976 | Bajek | G05D 21/02 422/62 |
| 5,159,957 | A * | 11/1992 | Hehl | B29C 45/72 62/201 |
| 5,742,064 | A | 4/1998 | Infante | |
| 6,050,283 | A * | 4/2000 | Hoffman | G05D 11/135 137/5 |
| 6,076,049 | A * | 6/2000 | Lievois | G01N 33/2847 702/100 |
| 6,089,282 | A * | 7/2000 | Spiegelman | H01J 9/52 141/66 |
| 6,112,134 | A * | 8/2000 | Terranova | G05D 11/132 700/239 |
| 6,321,782 | B1 * | 11/2001 | Hollister | F17C 13/025 137/557 |
| 6,446,875 | B1 * | 9/2002 | Brooks | E03C 1/05 236/12.12 |
| 6,676,024 | B1 * | 1/2004 | McNerney | G05D 23/1393 236/12.12 |
| 6,679,302 | B1 | 1/2004 | Mattingly et al. | |
| 6,966,326 | B2 * | 11/2005 | Murray | G05D 11/131 422/62 |
| 7,032,629 | B1 | 4/2006 | Mattingly et al. | |
| 7,631,671 | B2 | 12/2009 | Mattingly et al. | |
| 7,673,645 | B2 * | 3/2010 | Ding | G05D 11/132 137/870 |
| 9,388,350 | B2 * | 7/2016 | Buchanan | C10L 1/1824 |
| 9,494,948 | B2 | 11/2016 | Mattingly et al. | |
| 9,637,685 | B2 * | 5/2017 | Mattingly | C10C 3/005 |
| 11,022,986 | B2 | 6/2021 | Rady | |
| 2002/0046773 | A1 * | 4/2002 | Bishop | B63B 25/14 137/259 |
| 2004/0221889 | A1 * | 11/2004 | Dreyer | G05D 11/139 137/88 |
| 2005/0109402 | A1 * | 5/2005 | Lu | G05B 5/01 137/392 |
| 2006/0102133 | A1 * | 5/2006 | Callan | F01M 1/18 123/196 R |
| 2006/0213554 | A1 * | 9/2006 | Welch | G01N 33/2829 137/93 |
| 2006/0278281 | A1 | 12/2006 | Gunther et al. | |
| 2006/0278304 | A1 * | 12/2006 | Mattingly | G05D 11/131 141/100 |
| 2007/0001018 | A1 * | 1/2007 | Schmitt | G05D 23/1393 236/12.12 |
| 2007/0206436 | A1 * | 9/2007 | Niermeyer | B01F 35/831 366/160.1 |
| 2007/0246230 | A1 * | 10/2007 | Roberts | A62C 5/02 169/14 |
| 2008/0000529 | A1 * | 1/2008 | Lawrence Edwards | F17D 1/20 137/461 |
| 2008/0156077 | A1 * | 7/2008 | Flanders | F17D 5/00 700/282 |
| 2008/0165613 | A1 * | 7/2008 | Dykstra | G05D 11/135 700/285 |
| 2010/0212748 | A1 * | 8/2010 | Davidoff | F17D 5/02 137/487.5 |
| 2012/0238793 | A1 | 9/2012 | Cullinane et al. | |
| 2013/0291974 | A1 * | 11/2013 | Bourgeois | F17D 5/02 137/625.3 |
| 2014/0069516 | A1 * | 3/2014 | Shapira | F16K 19/006 137/88 |
| 2014/0152977 | A1 * | 6/2014 | Ranftl | G01N 21/61 356/51 |
| 2014/0195055 | A1 * | 7/2014 | Wadhwa | G05D 11/00 700/265 |
| 2015/0153746 | A1 * | 6/2015 | Lee | B67D 7/78 137/883 |
| 2016/0291610 | A1 * | 10/2016 | Kashima | G05D 11/132 |
| 2016/0320780 | A1 * | 11/2016 | Chebre | G05D 11/139 |
| 2017/0131728 | A1 * | 5/2017 | Lambert | G01N 21/359 |
| 2017/0166825 | A1 | 6/2017 | Mattingly et al. | |
| 2017/0173520 | A1 | 6/2017 | Acharya et al. | |
| 2019/0339724 | A1 | 11/2019 | Rady | |

\* cited by examiner

PIPELINE INTERCHANGE/TRANSMIX

CROSS-REFERENCE TO RELATED APPLICATIONS

This application is a continuation-in-part application which claims the benefit of and priority to U.S. patent application Ser. No. 16/391,817 filed Apr. 23, 2019 entitled "Pipeline Interchange" and Continuation-in-Part patent application Ser. No. 16/557,315 filed Aug. 30, 2019 entitled "Pipeline Interchange/Transmix," both of which are hereby incorporated by reference in their entirety.

STATEMENT REGARDING FEDERALLY SPONSORED RESEARCH OR DEVELOPMENT

None.

FIELD OF THE INVENTION

This invention relates to a pipeline interchange/transmix.

BACKGROUND OF THE INVENTION

Pipelines often transport physically and chemically different types of petroleum product in the same pipeline. In some pipeline systems the different types of petroleum products get blended together to achieve an optimal final petroleum product. For example, different pipelines might bring in different types of crude oil to be processed in a refinery and a refinery might have to manage Canadian crude, shale crude, and sweet crude all within the same day.

This situation adds extreme complexity to refineries as they must manage all of the different types of crude to make a standardized refined petroleum product. Unfortunately, due to all the different physical and chemical characteristics that are each unique to each of the crude products it is difficult to manage all of these different characteristics to product a standardized refined petroleum product. Different physical and chemical characteristics may require the refinery to handle the crude differently prior to being processed into a refined petroleum product.

In other types of pipeline systems, a pipeline operator sends different products in "batches" down a central pipeline that must be separated. For example, an operator might send gasoline for several hours, and then switch to jet fuels, before switching to diesel fuel. The process of tracking the customer's batch or product through the pipeline is done through analyzing the different products within a pipeline.

In situations where pipeline operators send different products through a central pipeline, the product is measured at the receipt point in the pipeline and again upon delivery to document the amount of product moved from point A to point B. Many pipeline systems require pipeline owners to meet defined common product specifications for each product shipped. This requires pipeline owners to regularly analyze many different properties of products in a refinery or a terminal. In these scenarios, a sample of product is analyzed either before entering the pipeline or during to give an analytical result. Once the area in which the sample is taken from reaches a splitter, the operation of the splitter is adjusted based on the properties of the refined product.

Current analytical techniques, in a pipeline, require that the sample of product are taken with a hydrometer and adhere to guidelines such as ASTM guidelines. To adhere to these guidelines pipeline operators must take the sample by either stopping the flow of a pipeline or taking a sample from a flowing pipeline. Stopping a pipeline is expensive and not ideal. Taking a sample from a flowing pipeline can mean large quantities of the refined product can flow through the pipeline prior to the analytical results being generated.

A pipeline interchange or transmix is generally known in the industry as a location where products that flow through a pipeline are either separated or combined. In the petroleum industry, this pipeline interchange generally consists of substantially horizontal pipes that operate within either a pipeline terminal, a refinery, a marine dock, or a rail terminal. Typically, one pipeline will be tasked with transporting various petroleum products and a method of separating the refined petroleum products within the pipeline to different pipelines or storage compartments is required. Alternatively, two or more pipelines will be tasked with transporting various petroleum products and a method of combining the petroleum products into one central pipeline is required.

There exists a need for a configuration that would allow a pipeline operator to obtain near instantaneous analytical results from samples of product and relay that information to either separate or combine petroleum products.

BRIEF SUMMARY OF THE DISCLOSURE

In one embodiment, a pipeline interchange is described where a first product flows through a first pipeline and a second product flows through a second pipeline. A pipeline interchange is connected downstream to both the first pipeline and the second pipeline, wherein the pipeline interchange blends the first product flowing through the first pipeline with the second product flowing through the second pipeline. A third pipeline is connected downstream to the pipeline interchange, wherein the third pipeline flows a blended product created from the blending of the first product and the second product in the pipeline interchange. An automated analyzer can be situated downstream of the pipeline interchange capable of physical and/or chemically analyzing the blended product and generating blended data. A data analyzer is also positioned to interpret the blended data and communicate adjustments to the flow of both the first product and the second product to achieve desired physical and/or chemical characteristics in the blended product.

In another embodiment, a pipeline interchange is described where a first product flows through a first pipeline and a second product flows through a second pipeline. In this embodiment, an optional first product automated analyzer is situated near the first pipeline to physical and/or chemically analyze the first product and generate first product data. Additionally, in this embodiment, an optional second product automated analyzer is situated near the second pipeline to physical and/or chemically analyze the second product and generate second product data. A pipeline interchange is connected downstream to both the first pipeline and the second pipeline, wherein the pipeline interchange blends the first product flowing through the first pipeline with the second product flowing through the second pipeline. A third pipeline is connected downstream to the pipeline interchange, wherein the third pipeline flows a blended product created from the blending of the first product and the second product in the pipeline interchange. An automated analyzer can be situated downstream of the pipeline interchange capable of physical and/or chemically analyzing the blended product and generating blended data. A data analyzer is also positioned to interpret the blended data; the first product data; and the second product data and communicate adjustments to the flow of both the first product and the second product to achieve desired physical and/or chemical characteristics in the blended product.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Figure 1:
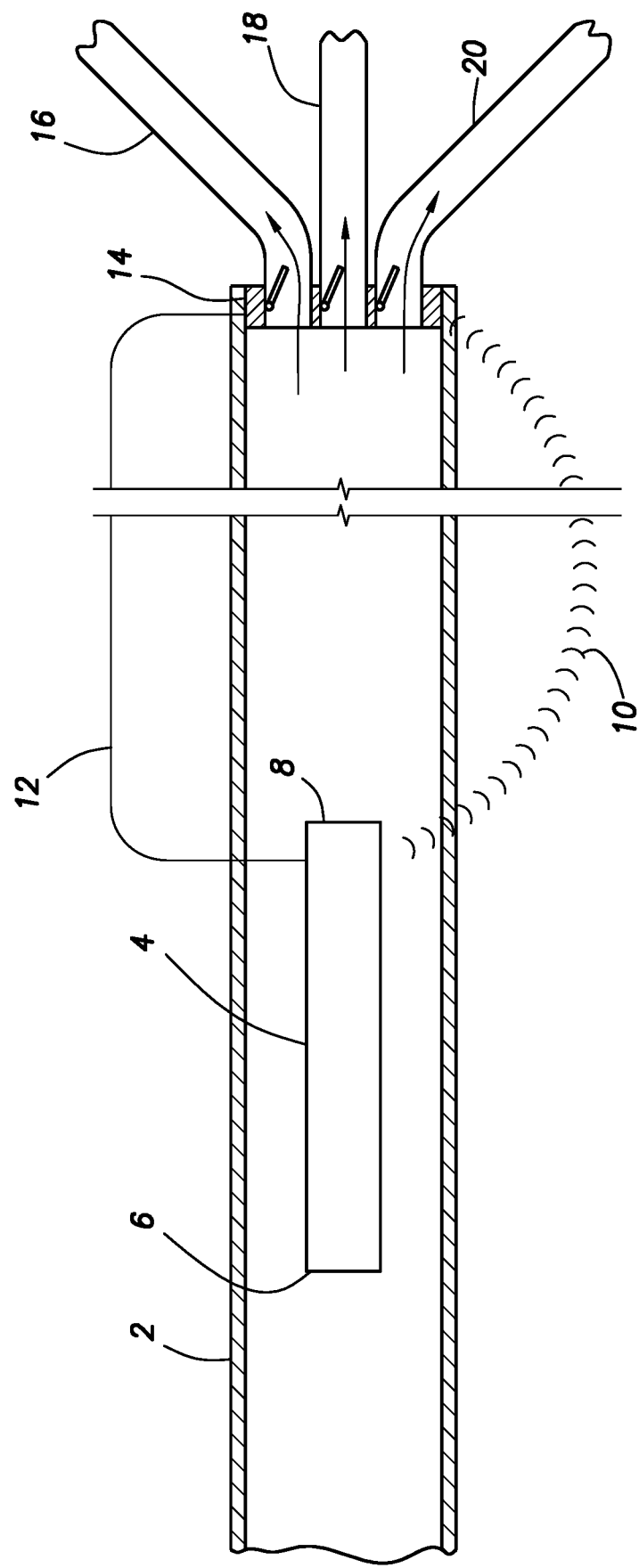
FIG. 1 depicts one embodiment of the pipeline interchange.

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

In one embodiment, a pipeline interchange flows a product through an upstream pipeline. An automated analyzer is connected to the upstream pipeline, wherein the automated analyzer analyzes a sample of the product, and wherein the analyzer is capable of analyzing different physical and/or chemical characteristics of the product and generating a data sample. An automatic splitter is then placed downstream of the automated slipstream analyzer. In this embodiment, the automatic splitter is capable of receiving and interpreting the data sample from the automated analyzer and directing the product into at least three different downstream pipelines, wherein at least one of the downstream pipelines is a transmix pipeline and wherein at least one of the downstream pipelines returns the product upstream of the automated analyzer.

In yet another embodiment, a pipeline interchange flows a refined petroleum product through an upstream pipeline. An automated analyzer comprising an inlet, a return and an analyzer, wherein the automated analyzer is used to collect a sample, analyze the sample of the refined petroleum product, and return the sample of the refined petroleum product flowing through the upstream pipeline, and wherein the analyzer is capable of analyzing different physical and/or chemical characteristics of the refined petroleum product. An automatic splitter is then placed downstream of the automated slipstream analyzer and generating a data sample. In this embodiment, the automatic splitter is capable of receiving and interpreting the data sample from the automated analyzer and directing the refined petroleum product into at least three different downstream pipelines, wherein at least one of the downstream pipelines is a transmix pipeline and wherein at least one of the downstream pipelines returns the refined petroleum product upstream of the automated analyzer.

In one embodiment, a pipeline interchange flows a product through an upstream pipeline. An automated analyzer is connected to the upstream pipeline to analyze different physical and/or chemically properties in the product and generate data from the product without extracting a sample from the upstream pipeline. An automatic splitter is placed downstream of the automated analyzer, capable of receiving and interpreting the data from the automated analyzer and directing the refined petroleum product into at least three different downstream pipelines, wherein at least one of the downstream pipelines is a transmix pipeline.

In yet another embodiment, a pipeline interchange flows a refined petroleum product through an upstream pipeline. An automated analyzer connected to the upstream pipeline wherein the automated analyzer physically and/or chemically analyzes the refined petroleum product and generates data from the refined petroleum product without extracting a sample from the upstream pipeline. An automatic splitter is placed downstream of the automated analyzer, capable of receiving and interpreting the data from the automated analyzer and directing the refined petroleum product into at least three different downstream pipelines, wherein at least one of the downstream pipelines is a transmix pipeline.

In one embodiment, the method begins by flowing a product stream through an upstream pipeline comprising a first product stream. The product stream is then continuously analyzed with an automated analyze to produce data. The first product stream downstream is then directed downstream of the automated analyzer to a downstream first product stream pipeline. The method then changes the product stream flowing through the upstream pipeline from the first product stream to a second product stream without purging the first product stream from the upstream pipeline, thereby creating a transmix product stream within the upstream pipeline wherein the transmix product stream comprises a mixture of the first product stream and the second product stream. The data from the automated analyzer is then analyzed with an automatic splitter, wherein the product stream flowing through the upstream pipeline no longer matches the physical and/or chemical characteristics of the first product stream. The automatic splitter then directs the transmix product stream downstream of the automatic splitter to a downstream transmix pipeline. As the data from the automated analyzer is still analyzed by the automatic splitter the product stream flowing through the upstream pipeline matches the physical and/or chemical characteristics of the second product stream. The automatic splitter then directs the second product stream downstream of the automatic splitter to a downstream second product stream pipeline.

In yet another embodiment, the method begins by flowing a product stream through an upstream pipeline comprising a first refined petroleum product stream. The product stream is then continuously analyzed with an automated analyze to produce data. The first refined petroleum product stream downstream is then directed downstream of the automated analyzer to a downstream first refined petroleum product stream pipeline. The method then changes the product stream flowing through the upstream pipeline from the first refined petroleum product stream to a second refined petroleum product stream without purging the first refined petroleum product stream from the upstream pipeline, thereby creating a transmix product stream within the upstream pipeline wherein the transmix product stream comprises a mixture of the first refined petroleum product stream and the second refined petroleum product stream. The data from the automated analyzer is then analyzed with an automatic splitter, wherein the product stream flowing through the upstream pipeline no longer matches the physical and/or chemical characteristics of the first refined petroleum product stream. The automatic splitter then directs the transmix product stream downstream of the automatic splitter to a downstream transmix pipeline. As the data from the automated analyzer is still analyzed by the automatic splitter the product stream flowing through the upstream pipeline matches the physical and/or chemical characteristics of the second refined petroleum product stream. The automatic splitter then directs the second refined petroleum product stream downstream of the automatic splitter to a downstream second refined petroleum product stream pipeline.

In one embodiment, a pipeline interchange is described where a first product flows through a first pipeline and a second product flows through a second pipeline. A pipeline interchange is connected downstream to both the first pipeline and the second pipeline, wherein the pipeline interchange blends the first product flowing through the first pipeline with the second product flowing through the second pipeline. A third pipeline is connected downstream to the pipeline interchange, wherein the third pipeline flows a blended product created from the blending of the first product and the second product in the pipeline interchange. An automated analyzer can be situated downstream of the pipeline interchange capable of physical and/or chemically analyzing the blended product and generating blended data. A data analyzer is also positioned to interpret the blended data and communicate adjustments to the flow of both the first product and the second product to achieve desired physical and/or chemical characteristics in the blended product.

In another embodiment, a pipeline interchange is described where a first product flows through a first pipeline and a second product flows through a second pipeline. In this embodiment, an optional first product automated analyzer is situated near the first pipeline to physical and/or chemically analyze the first product and generate first product data. Additionally, in this embodiment, an optional second product automated analyzer is situated near the second pipeline to physical and/or chemically analyze the second product and generate second product data. A pipeline interchange is connected downstream to both the first pipeline and the second pipeline, wherein the pipeline interchange blends the first product flowing through the first pipeline with the second product flowing through the second pipeline. A third pipeline is connected downstream to the pipeline interchange, wherein the third pipeline flows a blended product created from the blending of the first product and the second product in the pipeline interchange. An automated analyzer can be situated downstream of the pipeline interchange capable of physical and/or chemically analyzing the blended product and generating blended data. A data analyzer is also positioned to interpret the blended data; the first product data; and the second product data and communicate adjustments to the flow of both the first product and the second product to achieve desired physical and/or chemical characteristics in the blended product.

In one embodiment, a pipeline interchange is described where a first product flows through a first pipeline and a second product flows through a second pipeline. In this embodiment, a first product automated analyzer is situated near the first pipeline to physical and/or chemically analyze the first product and generate first product data. Additionally, in this embodiment, a second product automated analyzer is situated near the second pipeline to physical and/or chemically analyze the second product and generate second product data. A pipeline interchange is connected downstream to both the first pipeline and the second pipeline, wherein the pipeline interchange blends the first product flowing through the first pipeline with the second product flowing through the second pipeline. A third pipeline is connected downstream to the pipeline interchange, wherein the third pipeline flows a blended product created from the blending of the first product and the second product in the pipeline interchange. A data analyzer is also positioned to interpret the first product data and the second product data and communicate adjustments to the flow of both the first product and the second product to achieve desired physical and/or chemical characteristics in the blended product.

In another embodiment, a pipeline interchange is described where a first product flows through a first pipeline and a second product flows through a second pipeline. In this embodiment, a first product automated analyzer is situated near the first pipeline to physical and/or chemically analyze the first product and generate first product data. Additionally, in this embodiment, a second product automated analyzer is situated near the second pipeline to physical and/or chemically analyze the second product and generate second product data. A pipeline interchange is connected downstream to both the first pipeline and the second pipeline, wherein the pipeline interchange blends the first product flowing through the first pipeline with the second product flowing through the second pipeline. A third pipeline is connected downstream to the pipeline interchange, wherein the third pipeline flows a blended product created from the blending of the first product and the second product in the pipeline interchange. An optional automated analyzer can be situated downstream of the pipeline interchange capable of physical and/or chemically analyzing the blended product and generating blended data. A data analyzer is also positioned to interpret the blended data; the first product data; and the second product data and communicate adjustments to the flow of both the first product and the second product to achieve desired physical and/or chemical characteristics in the blended product.

In one embodiment, a process is taught where the process begins by flowing a first product through a first pipeline and flowing a second product through a second pipeline. The process then produces a blended product by mixing both the first product and the second product within a pipeline interchange which is connected downstream to both the first pipeline and the second pipeline. The blended product then flows from the pipeline interchange to a third pipeline that is connected downstream of pipeline interchange. The blended product is analyzed in the third pipeline with an automated analyzer that is capable of physical and/or chemically analyzing the blended product in the third pipeline and generating blended data. The blended data is then interpreted in a data analyzer by comparing the physical and/or chemical characteristics of the blended data to an optimal blended data and determining the adjustments in the flow of the first product and the flow of the second product to achieve optimal blended data from the blended product. The adjustments are then communicated to adjust the flow of the first product in the first pipeline and the flow of the second product in the second pipeline.

In another embodiment, a process is taught where the process begins by flowing a first product through a first pipeline and flowing a second product through a second pipeline. In this embodiment, the first product in the first pipeline is optionally analyzed with a first product automated analyzer that is capable of physical and/or chemically analyzing the first product in the first pipeline and generating a first product data. Additionally, in this embodiment, the second product in the second pipeline is optionally analyzed with a second product automated analyzer that is capable of physical and/or chemically analyzing the second product in the second pipeline and generating a second product data. The process then produces a blended product by mixing both the first product and the second product within a pipeline interchange which is connected downstream to both the first pipeline and the second pipeline. The blended product then flows from the pipeline interchange to a third pipeline that is connected downstream of pipeline interchange. The blended product is analyzed in the third pipeline with an automated analyzer that is capable of physical and/or chemically analyzing the blended product in the third pipeline and generating blended data. The first product data, second product data, and blended data is then interpreted in a data analyzer by comparing the physical and/or chemical characteristics of the blended data to an optimal blended data, the physical and/or chemical characteristics of the first data to an optimal first data, and the physical and/or chemical characteristics of the second data to an optimal second data. The data analyzer then determines the adjustments in the flow of the first product and the flow of the second product to achieve optimal blended data from the blended product. The adjustments are then communicated to adjust the flow of the first product in the first pipeline and the flow of the second product in the second pipeline In one embodiment, a process is taught where the process begins by flowing a first product through a first pipeline and flowing a second product through a second pipeline. In this embodiment, the first product in the first pipeline is analyzed with a first product automated analyzer that is capable of physical and/or chemically analyzing the first product in the first pipeline and generating a first product data. Additionally, in this embodiment, the second product in the second pipeline is analyzed with a second product automated analyzer that is capable of physical and/or chemically analyzing the second product in the second pipeline and generating a second product data. The process then produces a blended product by mixing both the first product and the second product within a pipeline interchange which is connected downstream to both the first pipeline and the second pipeline. The blended product then flows from the pipeline interchange to a third pipeline that is connected downstream of pipeline interchange. The first product data and the second product data is then interpreted in a data analyzer by comparing the physical and/or chemical characteristics of the physical and/or chemical characteristics of the first data to an optimal first data and the physical and/or chemical characteristics of the second data to an optimal second data. The data analyzer then determines the adjustments in the flow of the first product and the flow of the second product to achieve optimal blended data from the blended product. The adjustments are then communicated to adjust the flow of the first product in the first pipeline and the flow of the second product in the second pipeline.

In another embodiment, a process is taught where the process begins by flowing a first product through a first pipeline and flowing a second product through a second pipeline. In this embodiment, the first product in the first pipeline is analyzed with a first product automated analyzer that is capable of physical and/or chemically analyzing the first product in the first pipeline and generating a first product data. Additionally, in this embodiment, the second product in the second pipeline is analyzed with a second product automated analyzer that is capable of physical and/or chemically analyzing the second product in the second pipeline and generating a second product data. The process then produces a blended product by mixing both the first product and the second product within a pipeline interchange which is connected downstream to both the first pipeline and the second pipeline. The blended product then flows from the pipeline interchange to a third pipeline that is connected downstream of pipeline interchange. The blended product is then optionally analyzed in the third pipeline with an automated analyzer that is capable of physical and/or chemically analyzing the blended product in the third pipeline and generating blended data. The first product data, second product data, and blended data is then interpreted in a data analyzer by comparing the physical and/or chemical characteristics of the blended data to an optimal blended data, the physical and/or chemical characteristics of the first data to an optimal first data, and the physical and/or chemical characteristics of the second data to an optimal second data. The data analyzer then determines the adjustments in the flow of the first product and the flow of the second product to achieve optimal blended data from the blended product. The adjustments are then communicated to adjust the flow of the first product in the first pipeline and the flow of the second product in the second pipeline.

In one embodiment, an optional pipeline interchange automated analyzer can be placed within the pipeline interchange itself to measure the physical or chemical characteristics that flows through the pipeline interchange. In this embodiment, the data analyzer analyzes the data generated from the automated pipeline interchange automated analyzer.

In one embodiment, the flow of the first product in the first pipeline, the flow of the second product in the second pipeline or even the flow of the first product and the second product within the pipeline interchange can be controlled by valves. In some embodiments, the valves can be closed, open, or partially open to adjust the ratio of first product and second product in the blended product.

In some embodiments, the ratio of first product to second product in the blended product can be 100% first product to 0% second product, 0% first product to 100% second product. In other embodiments, the ratio can be anywhere from 0.1% to 99.9% first product to 0.1% to 99.9% second product.

In one embodiment, a programmable logic controller can be used to provide the control signals from the first product automated analyzer to the data analyzer, the second product automated analyzer to the data analyzer, and the automated analyzer to the data analyzer. Additionally, a programmable logic controller can be used to provide to the signal from the data analyzer to the first pipeline, second pipeline, and the pipeline interchange to adjust the flow of the first product or the second product to produce a blended product.

In one embodiment, a system is taught of separating transmix, gasoline, and diesel fuel from a refined petroleum product within a pipeline. In this embodiment, the transmix, gasoline, diesel fuel and refined petroleum product has optical properties which the system utilizes to assist in the distinguishing the features to separate the refined petroleum product. The system begins by having an automated slipstream analyzer in fluid connection with the refined petroleum product within the pipeline. A programmable logic controller is then used for governing the flow of refined petroleum product through the pipeline. A processor is then programmed to receive the refined petroleum product, estimate the flash temperature and provide a control signal to the programmable logic controller according to the maximum preprogrammed limits. In this embodiment, the programmable logic controller is configured to adjust the pipeline to provide an indication regarding when to direct the flow of the refined petroleum product into at least three downstream pipelines.

In yet another embodiment, a system is taught of blending transmix and diesel fuel from a refined petroleum product within a pipeline. In this embodiment, the transmix, gasoline fuel, diesel fuel, and refined petroleum product has optical properties which the system utilizes to assist in the distinguishing the features to blend the transmix and diesel fuel. The system begins by having a transmix pipeline and a diesel fuel pipeline in fluid connection downstream of a refined product pipeline. In this embodiment, an automated slipstream analyzer is in fluid connection with the refined petroleum product. A programmable logic controller is used for governing the flow of refined petroleum product towards the transmix pipeline, the diesel fuel pipeline, or the gasoline pipeline. Additionally, a processor is programmed to receive the refined petroleum product, calculate the amount of flash temperature of the refined petroleum product and provide a control signal to the programmable logic controller according to the preprogrammed limit for the blended diesel fuel. An automatic splitter, downstream of the automated slipstream analyzer, configured to adjust the flow of transmix, from either or both the transmix pipeline or the transmix reservoir, into the blended diesel fuel pipeline according to the preprogrammed limit for diesel fuel.

In another embodiment, a system is taught of blending transmix and gasoline fuel from a refined petroleum product within a pipeline. In this embodiment, the transmix, gasoline fuel, diesel fuel, and refined petroleum product has optical properties which the system utilizes to assist in the distinguishing the features to blend the transmix and gasoline fuel. The system begins by having a transmix pipeline, a diesel fuel pipeline, a gasoline pipeline, and a transmix reservoir in fluid connection downstream of a refined product pipeline, wherein the transmix pipeline flows into the transmix reservoir. In this embodiment, an automated slipstream analyzer in fluid connection with the refined petroleum product. A programmable logic controller is used for governing the flow of refined petroleum product towards the transmix pipeline, the diesel fuel pipeline, or the gasoline pipeline. Additionally, a processor is programmed to receive the refined petroleum product, calculate the amount of flash temperature of the refined petroleum product and provide a control signal to the programmable logic controller according to the preprogrammed limit for gasoline fuel. An automatic splitter, downstream of the automated slipstream analyzer, configured to adjust the flow of transmix, from either or both the transmix pipeline or the transmix reservoir, into the blended gasoline fuel pipeline according to the preprogrammed limit for gasoline fuel.

In yet another embodiment, a system is taught for blending transmix and diesel fuel from a refined petroleum product within a pipeline. In this embodiment, the transmix, gasoline fuel, diesel fuel, and refined petroleum product has optical properties which the system utilizes to assist in the distinguishing the features to blend the transmix and diesel fuel. The system begins by having a transmix pipeline, a diesel fuel pipeline, a gasoline pipeline, and a transmix reservoir in fluid connection downstream of a refined product pipeline, wherein the transmix pipeline flows into the transmix reservoir. In this embodiment, an automated slipstream analyzer is in fluid connection with the refined petroleum product. Additionally, a programmable logic controller for governing the flow of refined petroleum product towards the transmix pipeline, the diesel fuel pipeline, or the gasoline pipeline. A processor programmed to receive the refined petroleum product, calculate the amount of flash temperature of the refined petroleum product and provide a control signal to the programmable logic controller according to the preprogrammed limit for diesel fuel. An automatic splitter, downstream of the automated slipstream analyzer is configured to adjust the flow of transmix, from either or both the transmix pipeline or the transmix reservoir, into the diesel fuel pipeline according to the maximum preprogrammed limit for diesel fuel.

In another embodiment, a system is taught for blending transmix and gasoline fuel from a refined petroleum product within a pipeline. In this embodiment, the transmix, gasoline fuel, diesel fuel, and refined petroleum product has optical properties which the system utilizes to assist in the distinguishing the features to blend the transmix and gasoline fuel. The system begins by having a transmix pipeline, a diesel fuel pipeline, a gasoline pipeline, and a transmix reservoir in fluid connection downstream of a refined product pipeline, wherein the transmix pipeline flows into the transmix reservoir. In this embodiment, an automated slipstream analyzer is in fluid connection with the refined petroleum product. Additionally, a programmable logic controller for governing the flow of refined petroleum product towards the transmix pipeline, the diesel fuel pipeline, or the gasoline pipeline. A processor programmed to receive the refined petroleum product, calculate the amount of flash temperature of the refined petroleum product and provide a control signal to the programmable logic controller according to the preprogrammed limit for gasoline fuel. An automatic splitter, downstream of the automated slipstream analyzer is configured to adjust the flow of transmix, from either or both the transmix pipeline or the transmix reservoir, into the diesel fuel pipeline according to the maximum preprogrammed limit for gasoline fuel.

In one non-limiting embodiment, the methodology of measuring the flash temperature can be done via ASTM test method D86 or ASTM test method D93. In other embodiments, different optical test methods can be used to measure the flash temperature. In one embodiment, when using ASTM test method D86 to measure gasoline fuel the final boiling point can be around 437° F. In another embodiment, when using ASTM test method D93 to measure ultra low sulfur fuel or kerosene, the flash temperature is greater than 100.4° F. In yet another embodiment, when using ASTM test method D93 to measure ultra low sulfur diesel, the flash temperature is greater than 125.6° F. In an alternate embodiment the arrangement describes a pipeline interchange, wherein the pipeline interchange has a refined petroleum product flowing through an upstream pipeline. The pipeline interchange can also have an automated slipstream analyzer connected to the upstream pipeline comprising an inlet, a return and an analyzer. In this embodiment, the automated slipstream analyzer is used to collect a sample, analyze the sample, generate data from the sample and return the sample of the refined petroleum product flowing. In one non-limiting embodiment, the methodology of measuring the flash temperature can be done via ASTM test method D86 or ASTM test method D93. In other embodiments, different optical test methods can be used to measure the flash temperature. In one embodiment, when using ASTM test method D86 to measure gasoline fuel the final boiling point can be around 437° F. In another embodiment, when using ASTM test method D93 to measure ultra low sulfur fuel or kerosene, the flash temperature is greater than 100.4° F. In yet another embodiment, when using ASTM test method D93 to measure ultra low sulfur diesel, the flash temperature is greater than 125.6° F. In an alternate embodiment the arrangement describes a pipeline interchange, wherein the pipeline interchange has a refined petroleum product flowing through an upstream pipeline. The pipeline interchange can also have an automated slipstream analyzer connected to the upstream pipeline comprising an inlet, a return and an analyzer. In this embodiment, the automated slipstream analyzer is used to collect a sample, analyze the sample, generate data from the sample and return the sample of the refined petroleum product flowing.

In some embodiment, an upstream pipeline is generally defined as the pipeline upstream of the pipeline interchange and a downstream pipeline is generally defined as the pipeline downstream of the pipeline interchange.

In an alternate embodiment the different automated analyzers can also have an automated slipstream analyzer connected to the pipeline comprising an inlet, a return and an analyzer. In this embodiment, the automated slipstream analyzer is used to collect a sample, analyze the sample, generate data from the sample and return the sample of the products flowing through the different pipelines.

One embodiment describes a pipeline interchange, wherein the pipeline interchange has a refined petroleum product or crude petroleum product flowing through the pipeline. The pipeline interchange can also have an automated slipstream analyzer connected to the upstream pipeline comprising an inlet, a return and an analyzer. In this embodiment, the automated slipstream analyzer is used to collect a sample, analyze the sample, generate data from the sample and return the sample of the refined petroleum product flowing through the upstream pipeline.

When the pipeline interchange is used as a splitter, the pipeline interchange can have an automatic splitter, downstream of the automated slipstream analyzer, capable of receiving and interpreting the data from the automated slipstream analyzer and directing of directing the refined petroleum product into at least three different downstream pipelines, wherein at least one of the downstream pipelines is an intermix pipeline.

In this embodiment, an upstream pipeline is generally defined as the pipeline upstream of the pipeline interchange and a downstream pipeline is generally defined as the pipeline downstream of the pipeline interchange.

When the pipeline interchange is used as a blender, the pipeline interchange can have both a first pipeline and a second pipeline, both upstream pipelines, placed upstream of the pipeline interchange. The third pipeline, or downstream pipeline, can be placed downstream of the pipeline interchange. The pipeline interchange in this embodiment is capable of blending the products that flow in the first pipeline and the second pipeline together to generate a blended product in the third pipeline.

In one embodiment, the pipeline interchange is an integral part of a pipeline terminal or a refinery. A pipeline interchange is generally thought of as a place where different pipelines can either intersect or diverge. The size of the upstream pipeline and downstream pipelines can vary based upon the products they are transporting. In one embodiment, the upstream pipeline and the downstream pipeline can range from about 4 inches in diameter to about 48 inches in diameter. These pipelines can either flow downstream of the pipeline interchange into other pipelines, into storage containers or storage tanks, into marine vessels, or into rail cars. These medians can also include an intermix. In one embodiment, at least three different downstream pipelines can be connected to pipeline storage tanks or intermix storage tanks.

In other embodiments, there can be two different upstream or downstream pipelines, three different upstream or downstream pipelines, four different upstream or downstream pipelines, five different upstream or downstream pipelines, six different upstream or downstream pipelines or more. The number of different upstream or downstream pipelines will depend upon the different types of products flowing into the pipeline interchange. In other embodiments, the one of the downstream pipelines can be dedicated for contaminates. In yet another embodiment, the downstream and upstream pipelines can be interchangeable for their uses.

In other embodiments, there can be two different downstream pipelines, three different downstream pipelines, four different downstream pipelines, five different downstream pipelines, six different downstream pipelines or more. The number of different downstream pipelines will depend upon the different types of refined petroleum products flowing through the upstream pipeline. In other embodiments, the one of the downstream pipelines can be dedicated for contaminates. In yet another embodiment, the downstream pipelines can be interchangeable for their uses.

The refined product that flows through the pipelines can be any liquid or gaseous product that can be derived from crude oils through processes such as catalytic cracking and fractional distillation. These products can have physical and chemical characteristics that differ according to the type of crude oil and subsequent refining processes. Different types of product streams can be flowed through the pipelines including gasoline, diesel fuels, jet fuels, naphtha, marine gas oils, liquefied petroleum gasses, kerosene, lubricating oils and different types of fuel oils such as No. 2, No. 4, No. 5, and No. 6. In some embodiments, two different products can flow through the pipeline to have a first product stream and a second product stream, or a first refined product stream and a second refined product stream. In one embodiment, the first product stream and the second product stream is chemically distinctive from each other.

It is envisioned, in one embodiment, that the flow of the refined product would not be decreased when flowing through the pipeline interchange.

In one embodiment of the invention the analyzer is an optical analyzer. Unlike hydrometers that manually measure the density of the refined petroleum product it is envisioned that the pipeline interchange will utilize a continuous or periodic optical analyzer. In one embodiment, the pipeline interchange operates without a hydrometer. In a non-limiting embodiment, types of analyzers that can be used include, near-infrared analyzers, mid-infrared analyzers, far-infrared analyzer, Raman analyzer, acoustic analyzer, UV-visible analyzer, density analyzer, NMR analyzer, viscometer analyzer, terahertz spectroscopy analyzer, conductivity analyzer, pH analyzer, mass spectrometry analyzer, turbidity analyzer, particle size analyzer, electron loss spectroscopy analyzer, fluorescence analyzer, micro- and nano-electromechanical systems analyzers, chromatography analyzer, electrophoresis analyzer, microwave resonance analyzer, cavity-ringdown analyzer, cavity-enhanced analyzer, dielectric spectroscopy, surface plasmon resonance analyzer, quartz crystal microbalance analyzer, biosensing analyzers, time resolved spectrometers, and micro total analytical systems analyzer. The quantitative data generated by these analyzers can include data for premium gasoline, jet fuel, diesel fuel and unleaded gasoline.

In one embodiment, the analyzers can be used to analyze contaminants in the refined product. These contaminants can be compounds such as: benzene, toluene, ethylbenzene, xylenes, methyl tertiary butyl ethers, sulfur, vanadium, iron, zinc, lead scavengers, moisture, organic-based additives, or even biomaterial. In other embodiments, the optical analyzer can be used to analyze optical properties of refined products or refined petroleum products such as: flash temperature octane numbers, research octane numbers, motor octane numbers, antiknock index, boiling point, density, viscosity, molecular type compositions, elemental analysis, freezing point, carbon residue, pour point, cloud point, vapor pressure, reid vapor pressure, flammability range, wax and asphaltene contents, cetane number, aniline point, and carbon-to-hydrogen ratios.

By utilizing analyzers, the automatic splitter and/or data analyzer will be able to receive rapid and reliable data regarding the composition of the refined petroleum product that is flowing through the pipeline. Additionally, the samples taken and returned to the pipeline by the optical analyzers allow the petroleum product to be reused instead of conventional hand measurement methods that can modify the petroleum product and therefore make it unsuitable of being returned to the pipeline or being used as a conventional fuel. Depending on the physical or chemical method used cannot take samples.

In alternate embodiments it is possible to place multiple analyzers along a pipeline, either the upstream pipelines, downstream pipelines, first pipeline, second pipeline, or third pipeline. The multiple analyzers will provide data to the automatic splitter and/or data analyzer to analyzer the data. It is theorized by placing multiple analyzers the automatic splitter and/or data analyzer would have additional data to generate instructions and adjustments to the pipeline interchange system thereby producing more accurate results.

In one embodiment, automatic splitter comprises both a physical device capable of directing the product to the different pipelines, such as downstream pipelines, and a data analyzer capable of analyzing the data. In some embodiments, the data analyzer is physically located at a different location than the automatic splitter.

It is theorized that by using a continuous or periodic analyzer that the data generated can be received and interpreted by the automatic splitter and/or data analyzer is faster than conventional methods. The automatic splitter and/or data analyzer can then be able to determine the precise moment the refined petroleum product changes from one type of petroleum product to an intermix/transmix and from the intermix/transmix to another type of petroleum product. Intermix/transmix is defined as a random mixture of on-specification fuels that due to their mixing no longer meet a specific fuel specification, such intermix/transmix fluids can be directed to an intermix/transmix pipeline, which can be connected to an intermix/transmix storage tank, which will be redistributed back to a refinery to generate petroleum products that meet product specification requirements.

In one example the analyzer is an infrared analyzer such as midinfrared, near-infrared analyzer, far infrared. These types of analyzers are typically spectroscopic using technical designs such as dispersive, fourier-transform, microelectromechanical systems, acousto-optic tunable filters, and super-luminescent LED's. The analytical information that these types of analyzers usually obtain are molecular vibrations from absorbance/transmittance of wavenumbers. Additionally, these types of analyzers can be obtained from samples withdrawn from the pipeline, or from probes with direct contact with the product in the pipeline.

In another example the analyzer is a Raman analyzer. These types of analyzers are typically spectroscopic using technical designs such as dispersive, interferometric, fourier-transform, czerny-turner, and process micro spectroscopy. The analytical information that these types of analyzers usually obtain are molecular scattering of wavenumbers or intensity. Additionally, these types of analyzers can be obtained from samples withdrawn from the pipeline, or from probes with direct contact with the product in the pipeline.

In another example the analyzer is an acoustic analyzer. These types of analyzers are typically sensors that use acoustics such as active, passive, transverse, and longitudinal. The analytical information that these types of analyzers usually obtain are acoustic emissions and changes in velocity and/or amplitude of mechanical waves such as vibration, ultrasonic, infrasonic, subsonic, and supersonic. These phases or frequencies can be obtained from probes with direct contact with the product in the pipeline or by external clamp-on to the pipeline using straps, glue, screw, magnet, tape, etc. such that the incident wave penetrates through the pipe wall.

In another example the analyzer is a UV-visible analyzer. These types of analyzers are typically spectroscopic that measure electronic transitions of absorbance or transmittance of wavelengths. Additionally, these types of analyzers can be obtained from samples withdrawn from the pipeline.

In another example the analyzer is a density meter. These types of analyzers are typically gravimetric using technical designs such as vibrating elements. The analytical information that these types of analyzers typically obtain are density information from vibration frequency which is generally inversely proportional to density. Additionally, these types of analyzers can be obtained from samples withdrawn from the pipeline, or from probes with direct contact with the product in the pipeline.

In another example the analyzer is an NMR analyzer. These types of analyzers are typically spectroscopic using technical designs such as time-domain or high resolution. The analytical information that these types of analyzers typically obtain are absolute signal intensities, free induction decays, and chemical shifts. These intensity/chemical shift signals can be obtained from probes with direct contact with the product, using devices that withdraw samples from the pipeline to the instrument or using a configuration where samples are collected and analyzed on the instrument which is placed in close proximity to the pipeline.

In another example the analyzer is a viscometer. These types of analyzers are typically viscometric using technical designs such as vibrating elements. The analytical information that these types of analyzers typically obtain include the natural frequency of vibration changes that occur with the fluid viscosity. The bandwidth of the vibrating elements can be converted to a viscosity measurement using calibration coefficients. These frequencies can typically be obtained from probes with direct contact with the product in the pipeline.

In another example the analyzer is a terahertz spectroscopy analyzer. These types of analyzers typically utilize spectroscopic analysis to measure the rotational and vibrational transitions or molecular vibrational or torsional modes in condensed phase materials. The signals from this type of analyzer are typically absorbance or photocurrent intensity and can be obtained from either sample withdrawn from the pipeline, or from probes with direct contact with the product in the pipeline In other embodiments, the data obtains from the analyzers can be interpreted by using chemometrics. Chemometrics would assist the method by modelling and correlating underlying relationships, extracting and enhancing subtle but informative chemical features, recognizing signal patterns and fingerprints, and predicting new properties using analytical signals that are generated from the analyzers within the method. In one embodiment, the automatic splitter can analyze the data using chemometrics to determine the modelling relationship of the product or refined petroleum product to the data. This modelling relationship can be continuously updated as additional data is provided by the automated analyzer. Having the automatic splitter to analyze the data chemometrically would allow the automatic splitter to more clearly define the chemical characteristics that distinguish a first product stream to a second product stream, or from a first refined product stream to a second refined product stream.

In other embodiments, it is envisioned that automatic splitter can then be able to determine the precise moment the refined petroleum product changes from one type of petroleum product to one that contains contaminates. The automatic splitter then would direct the contaminated refined product to a pipeline that can be redistributed back to a refinery instead of to storage tanks for consumer use.

The automatic splitter can be from 1 meter to 500 meters downstream of the automated slipstream analyzer. In one embodiment, the automatic splitter can be up to 1 kilometer, 2 kilometers or even 5 kilometers downstream of the automated slipstream analyzer. The automatic splitter can be any splitter capable of directing the flow of the upstream pipeline into the different downstream pipelines. This can consist of a valve on each of the downstream pipelines or a central splitter used to direct the flow of fluid into one or more of the downstream pipelines.

In one embodiment, the automated slipstream analyzer is located inline of the upstream pipeline. As shown in FIG. 1, a side profile of an upstream pipeline 2 is shown with an automated slipstream analyzer 4 deposed within. The automated slipstream analyzer has an inlet 6 capable of collecting a sample and a return 8 capable of returning the sample of refined petroleum product flowing through the upstream pipeline. The automated slipstream analyzer can analyze the sample collected from the inlet and generate data from the sample. The data generated from the automated slipstream analyzer can be transferred wirelessly 10 or by a wired connection 12 to an automatic splitter 14 located downstream of the automated slipstream analyzer. As depicted in this embodiment, automatic splitter comprises a valve on each of the downstream pipelines, in other embodiments this could be different. In one embodiment as shown in FIG. 1, the automatic splitter is able to direct the refined petroleum product into at least three different downstream pipelines 16, 18 and 20.

As depicted in FIG. 1, the automated slipstream analyzer is placed in the center of the upstream pipeline. It is understood that in different embodiments the automated slipstream analyzer can be placed anywhere within the upstream pipeline capable of collecting a sample of the refined petroleum product.

Figure 2:
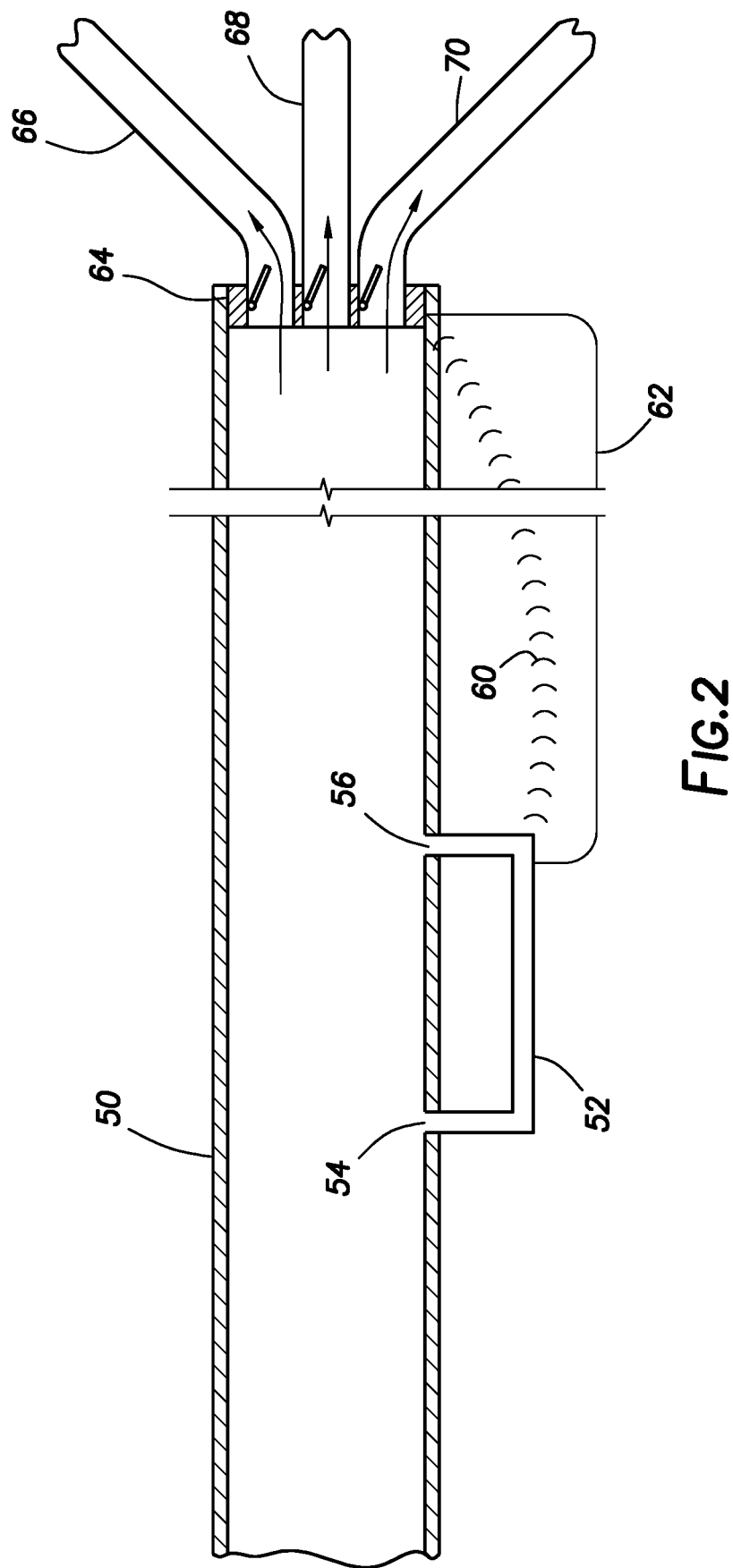
FIG. 2 depicts one embodiment of the pipeline interchange.

In another embodiment, the automated slipstream analyzer operates as a sample loop adjacent to the upstream pipeline. As shown in FIG. 2, upstream pipeline 50 has an automated slipstream analyzer 52 connected to the pipeline. The automated slipstream analyzer has an inlet 54 capable of collecting a sample and a return 58 capable of returning the sample of refined petroleum product flowing through the upstream pipeline. The inlet can be regulated to be a continuous flow or intermittent based on user needs. The automated slipstream analyzer can analyze the sample collected from the inlet and generate data from this sample. The data generated form the automated slipstream analyzer can be transferred wirelessly 60 or by a wired connection 62 to an automatic splitter 64 located downstream of the automated slipstream analyzer. As depicted in this embodiment, automatic splitter comprises a valve on each of the downstream pipelines, in other embodiments this could be different. In one embodiment as shown in FIG. 2, the automatic splitter is able to direct the refined petroleum product into at least three different downstream pipelines 66, 68 and 70.

Figure 3:
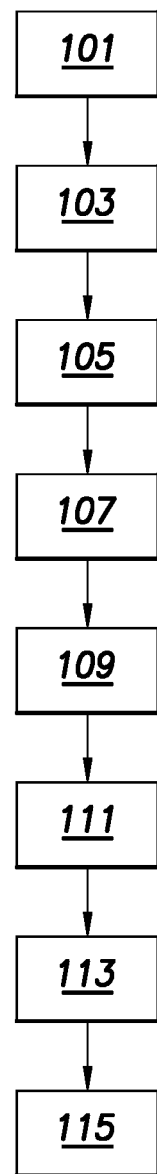
FIG. 3 depicts one embodiment of the process.

In one embodiment, a method is taught as shown in FIG. 3. The method begins by flowing a product stream through an upstream pipeline comprising a first product stream 101. The product stream is then continuously or periodically analyzed with an automated analyzer to produce data 103. The first product stream downstream is then directed downstream of the automated analyzer to a downstream first product stream pipeline 105. The method then changes the product stream flowing through the upstream pipeline from the first product stream to a second product stream without purging the first product stream from the upstream pipeline 107, thereby creating a transmix product stream within the upstream pipeline wherein the transmix product stream comprises a mixture of the first product stream and the second product stream. The data from the automated analyzer is then analyzed with an automatic splitter, wherein the product stream flowing through the upstream pipeline no longer matches the chemical characteristics of the first product stream 109. The automatic splitter then directs the transmix product stream downstream of the automatic splitter to a downstream transmix pipeline 111. As the data from the automated analyzer is still analyzed by the automatic splitter the product stream flowing through the upstream pipeline matches the chemical characteristics of the second product stream 113. The automatic splitter then directs the second product stream downstream of the automatic splitter to a downstream second product stream pipeline 115.

Figure 4:
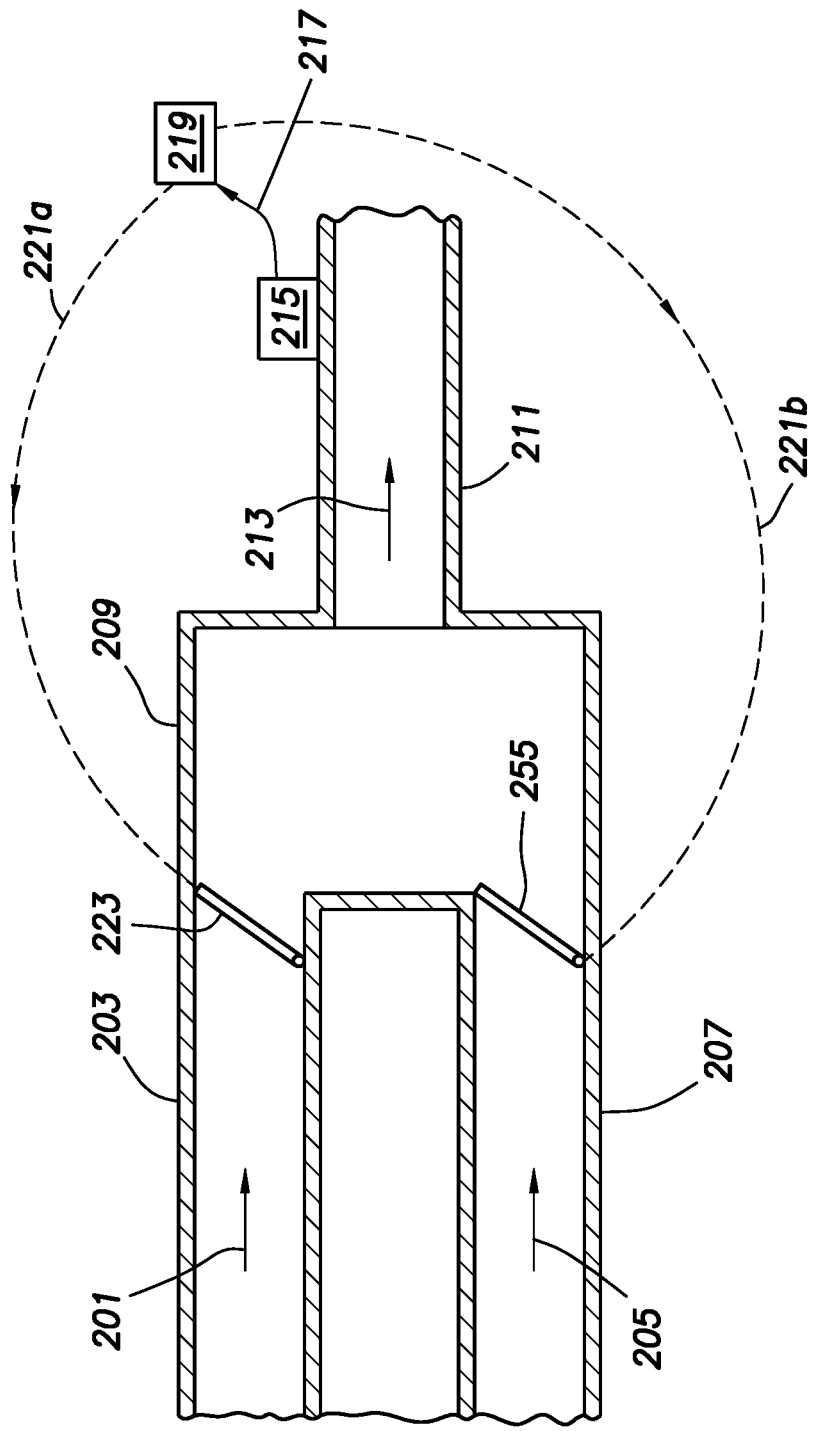
FIG. 4 depicts one embodiment of the pipeline interchange.

In another embodiment, a pipeline interchange is shown in FIG. 4. In this embodiment, a first product 201 flows through a first pipeline 203 and a second product 205 flows through a second pipeline 207. A pipeline interchange 209 is connected downstream to both the first pipeline and the second pipeline, wherein the pipeline interchange blends the first product flowing through the first pipeline with the second product flowing through the second pipeline. A third pipeline 211 connected downstream to the pipeline interchange, wherein the third pipeline flows a blended product 213 created from the blending of the first product and the second product in the pipeline interchange. An automated analyzer 215 is situated downstream of the pipeline interchange capable of physically or chemically analyzing the blended product in the third pipeline and generating blended data 217. In this embodiment, a data analyzer 219 is capable of receiving and interpreting the blended data and communicate 221a and 221b adjustments to values 223 and 225 situated in the first pipeline and the second pipeline. These values ensure that the flow of the first product and the second product are in the proper ratio to achieve desired physical or chemical characteristics in the blended product.

Figure 5:
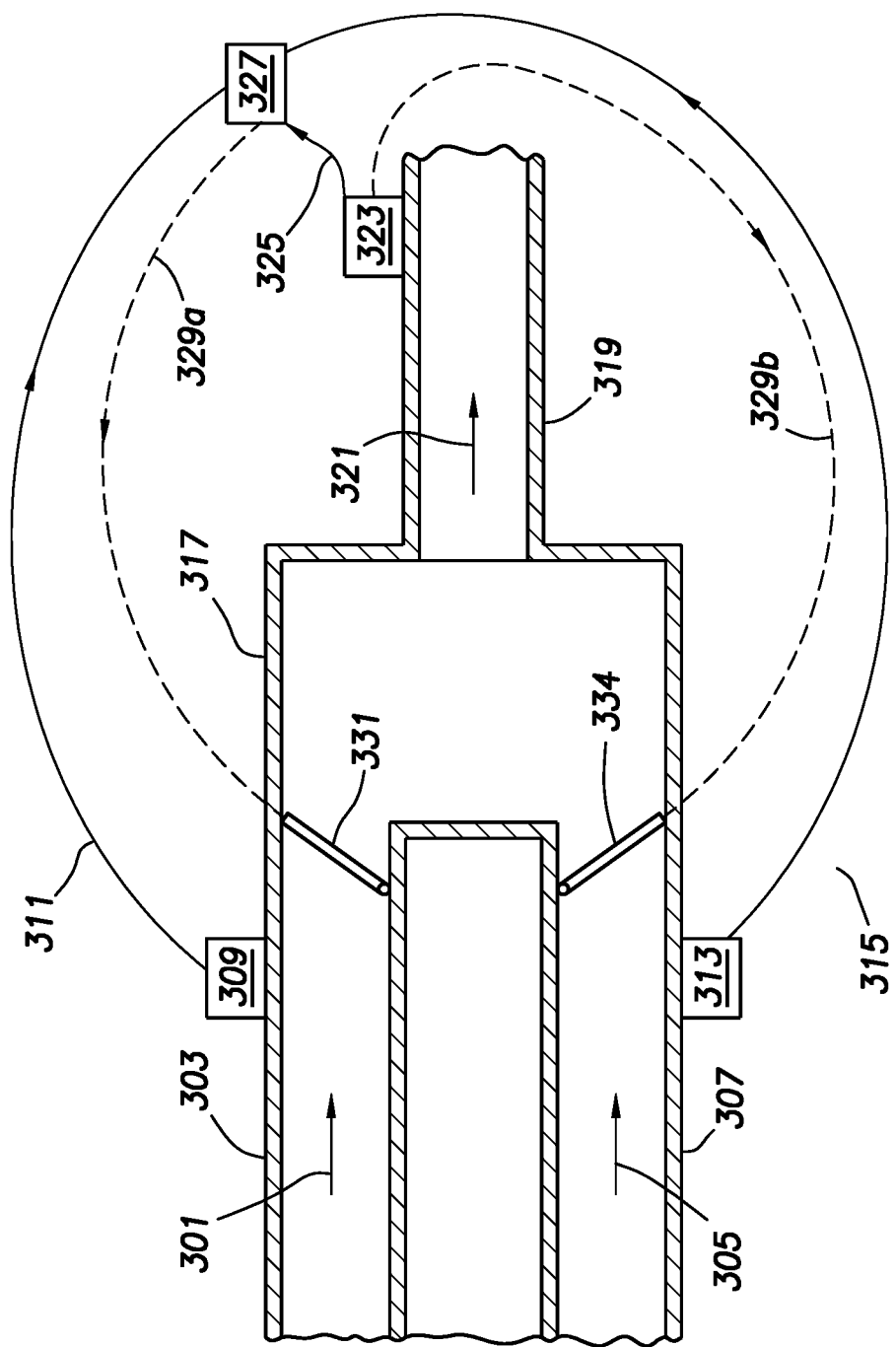
FIG. 5 depicts one embodiment of the pipeline interchange.

In yet another embodiment, a pipeline interchange is shown in FIG. 5. In this embodiment, a first product 301 flows through a first pipeline 303 and a second product 305 flows through a second pipeline 307. In this embodiment, an optional first product automated analyzer 309 is situated near the first pipeline to physically or chemically analyze the first product and generate first product data 311. Additionally, an optional second product automated analyzer 313 is situated near the second pipeline to physically or chemically analyze the second product and generate second product data 315. A pipeline interchange 317 is connected downstream to both the first pipeline and the second pipeline, wherein the pipeline interchange blends the first product flowing through the first pipeline with the second product flowing through the second pipeline. A third pipeline 319 connected downstream to the pipeline interchange, wherein the third pipeline flows a blended product 321 created from the blending of the first product and the second product in the pipeline interchange. An automated analyzer 323 is situated downstream of the pipeline interchange capable of physically or chemically analyzing the blended product in the third pipeline and generating blended data 325. In this embodiment, a data analyzer 327 is capable of receiving and interpreting the blended data, first product data, and second product data and communicate 329a and 329b adjustments to values 331 and 334 situated in the first pipeline and the second pipeline. These values ensure that the flow of the first product and the second product are in the proper ratio to achieve desired physical or chemical characteristics in the blended product.

Figure 6:
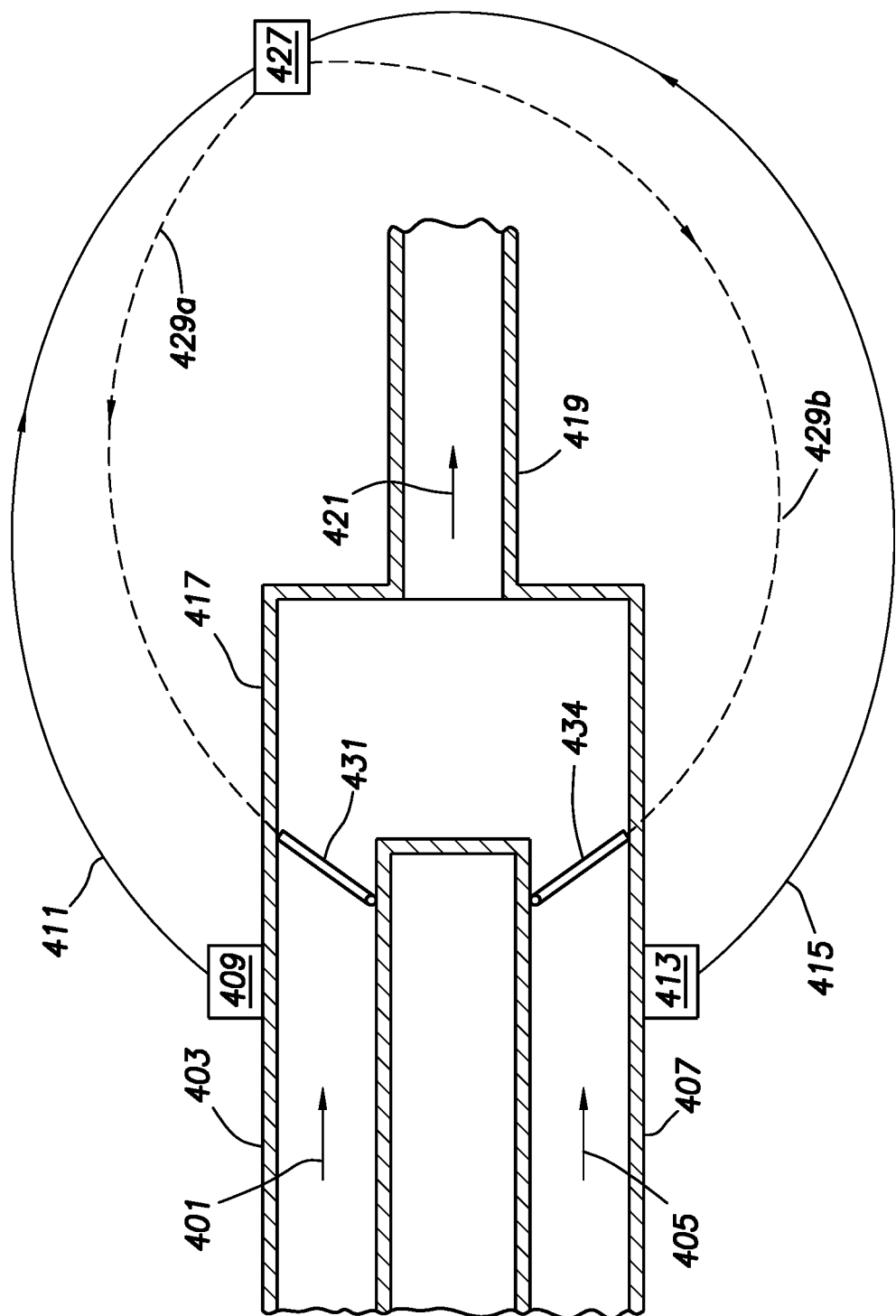
FIG. 6 depicts one embodiment of the pipeline interchange.

In one embodiment, a pipeline interchange is shown in FIG. 6. In this embodiment, a first product 401 flows through a first pipeline 403 and a second product 405 flows through a second pipeline 407. In this embodiment, a first product automated analyzer 409 is situated near the first pipeline to physically or chemically analyze the first product and generate first product data 411. Additionally, a second product automated analyzer 413 is situated near the second pipeline to physically or chemically analyze the second product and generate second product data 415. A pipeline interchange 417 is connected downstream to both the first pipeline and the second pipeline, wherein the pipeline interchange blends the first product flowing through the first pipeline with the second product flowing through the second pipeline. A third pipeline 419 connected downstream to the pipeline interchange, wherein the third pipeline flows a blended product 421 created from the blending of the first product and the second product in the pipeline interchange. In this embodiment, a data analyzer 427 is capable of receiving and interpreting the blended data, first product data, and second product data and communicate 429a and 429b adjustments to values 431 and 434 situated in the first pipeline and the second pipeline. These values ensure that the flow of the first product and the second product are in the proper ratio to achieve desired physical or chemical characteristics in the blended product.

Figure 7:
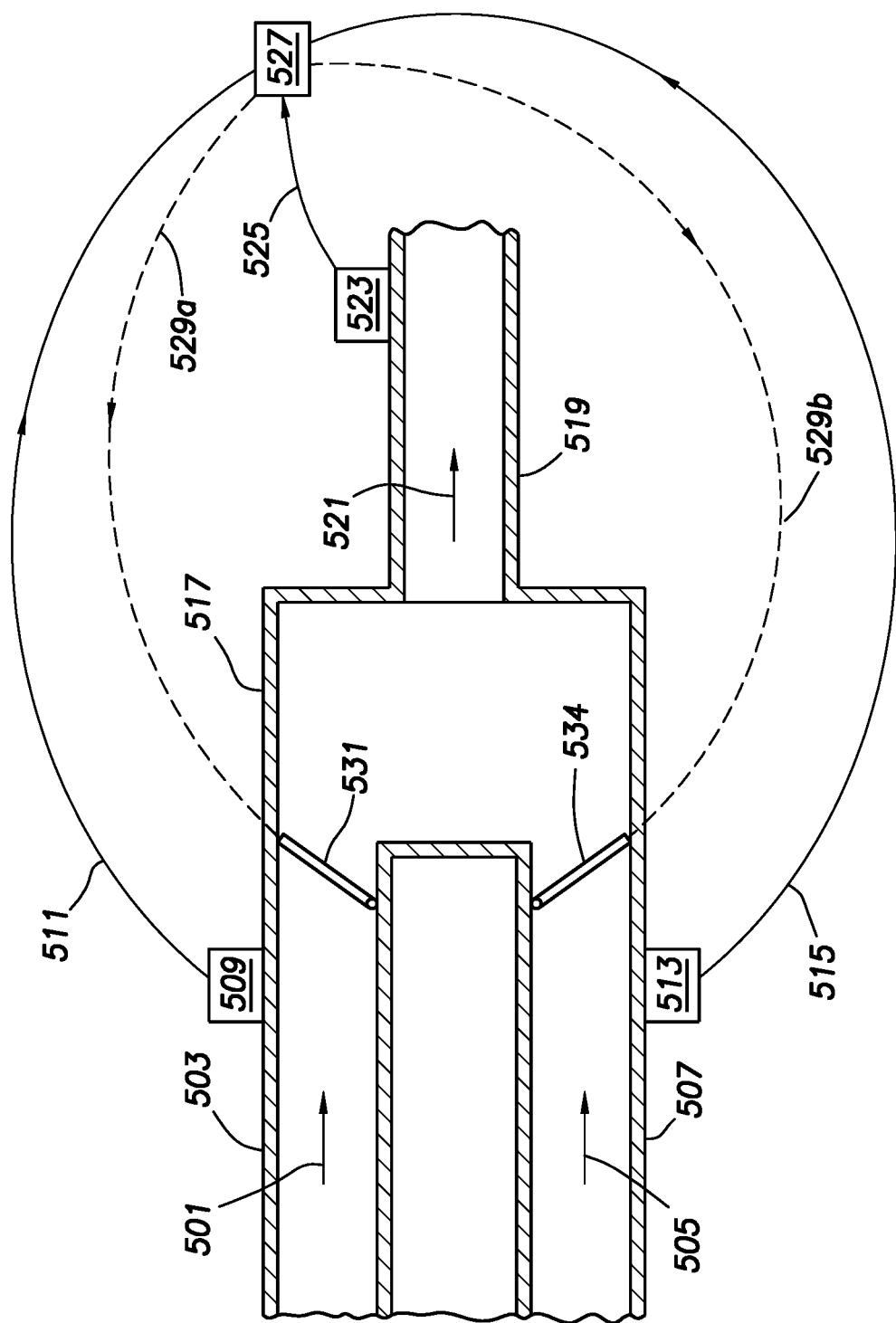
FIG. 7 depicts one embodiment of the pipeline interchange.

In another embodiment, a pipeline interchange is shown in FIG. 7. In this embodiment, a first product 501 flows through a first pipeline 503 and a second product 505 flows through a second pipeline 507. In this embodiment, a first product automated analyzer 409 is situated near the first pipeline to physically or chemically analyze the first product and generate first product data 511. Additionally, a second product automated analyzer 513 is situated near the second pipeline to physically or chemically analyze the second product and generate second product data 515. A pipeline interchange 517 is connected downstream to both the first pipeline and the second pipeline, wherein the pipeline interchange blends the first product flowing through the first pipeline with the second product flowing through the second pipeline. A third pipeline 519 connected downstream to the pipeline interchange, wherein the third pipeline flows a blended product 521 created from the blending of the first product and the second product in the pipeline interchange. An optional automated analyzer 523 is situated downstream of the pipeline interchange capable of physically or chemically analyzing the blended product in the third pipeline and generating blended data 525. In this embodiment, a data analyzer 527 is capable of receiving and interpreting the blended data, first product data, and second product data and communicate 529a and 529b adjustments to values 531 and 534 situated in the first pipeline and the second pipeline. These values ensure that the flow of the first product and the second product are in the proper ratio to achieve desired physical or chemical characteristics in the blended product.

In alternative scenarios, it is also possible that the data analyzer communicates adjustments to a pipeline interchange, wherein the pipeline interchange has valves within it capable of controlling the flow of the first product and the second product to produce a blended product.

Figure 8:
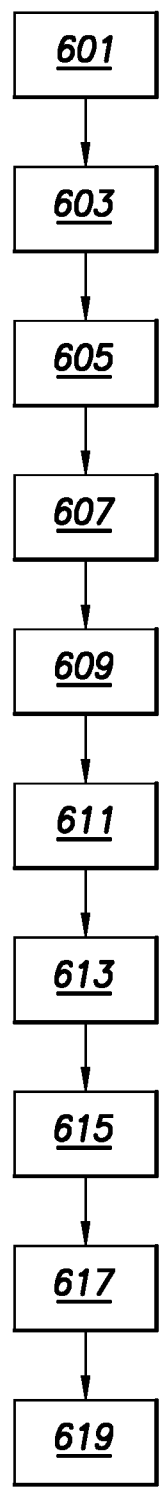
FIG. 8 depicts one embodiment of the process.

In one process embodiment, as shown in FIG. 8, the process begins by flowing a first product through a first pipeline 601. The process then can optionally analyze the first product in the first pipeline with a first product automated analyzer that is capable of physically or chemically analyzing the first product in the first pipeline and generating a first product data 603. The process can then flow a second product through a second pipeline 605. The process can then optionally analyze the second product in the second pipeline with a second product automated analyzer that is capable of physically or chemically analyzing the second product in the second pipeline and generating a second product data 607. A blended product can then be produced by mixing both the first product and the second product within a pipeline interchange which is connected downstream to both the first pipeline and the second pipeline 609. The blended product can the flow from the pipeline interchange to a third pipeline that is connected downstream of pipeline interchange 611. The blended product is then analyzed in the third pipeline with an automated analyzer that is capable of physically or chemically analyzing the blended product in the third pipeline and generating blended data 613. The first product data, the second product data, and the blended data are then interpreted in a data analyzer by comparing the physical or chemical characteristics of the blended data to an optimal blended data, the physical or chemical characteristics of the first data to an optimal first data, the physical or chemical characteristics of the second data to an optimal second data 615. The data analyzer can also determine the adjustments in the flow of the first product and the flow of the second product to achieve optimal first data, optimal second data, and optimal blended data 617. The adjustments can then be communicated in the flow of the first product in the first pipeline and the flow of the second product in the second pipeline from the data analyzer 619.

Figure 9:
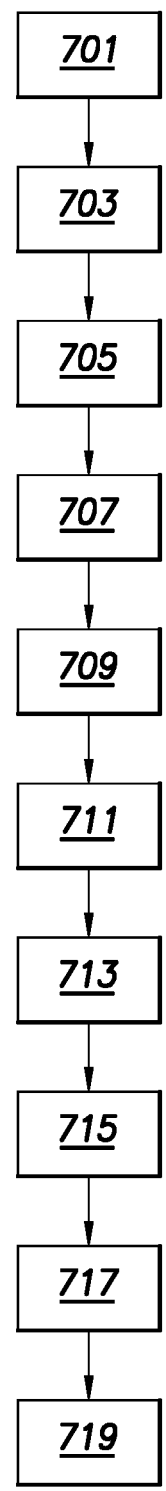
FIG. 9 depicts one embodiment of the process.

In yet another process embodiment, as shown in FIG. 9, the process begins by flowing a first product through a first pipeline 701. The process then can analyze the first product in the first pipeline with a first product automated analyzer that is capable of physically or chemically analyzing the first product in the first pipeline and generating a first product data 703. The process can then flow a second product through a second pipeline 705. The process can then analyze the second product in the second pipeline with a second product automated analyzer that is capable of physically or chemically analyzing the second product in the second pipeline and generating a second product data 707. A blended product can then be produced by mixing both the first product and the second product within a pipeline interchange which is connected downstream to both the first pipeline and the second pipeline 709. The blended product can the flow from the pipeline interchange to a third pipeline that is connected downstream of pipeline interchange 711. The blended product is then be optionally analyzed in the third pipeline with an automated analyzer that is capable of physically or chemically analyzing the blended product in the third pipeline and generating blended data 713. The first product data, the second product data, and the blended data are then interpreted in a data analyzer by comparing the physical or chemical characteristics of the blended data to an optimal blended data, the physical or chemical characteristics of the first data to an optimal first data, the physical or chemical characteristics of the second data to an optimal second data 715. The data analyzer can also determine the adjustments in the flow of the first product and the flow of the second product to achieve optimal first data, optimal second data, and optimal blended data 717. The adjustments can then be communicated in the flow of the first product in the first pipeline and the flow of the second product in the second pipeline from the data analyzer 719.

Certain embodiments of the inventive system and method comprise a computing device configured to receive data from the automated analyzer. In general, the computing device serves as an interface that receives and processes the spectral data received from the automated analyzer, then sends a signal/command to the automatic splitter to control its operation. In some embodiments, the computing device may be physically combined with, or immediately adjacent to, the either automated analyzer or the automatic splitter. However, there is no specific requirement for such physical integration and the computing device can optionally be located at any physical location within the system that allows it to be configured to receive data from the automated analyzer and output signals that control operation of the automatic splitter.

The computing device comprises a microprocessor with memory that contains programming. The programming is configured to provide instructions to the microprocessor to mathematically transform the spectral data received by the computing device to produce wavelet coefficients data according to wavelet theory by applying a mother wavelet consisting of a member of the Symlet family of mother wavelets (at the third level of decomposition or greater). The programming is additionally configured to provide instructions to the microprocessor comprising a trained genetic algorithm that can classify the wavelets coefficients data (representing a given optical or NMR spectrum) into one of two or more groups based upon one or more spectral features recognized by the trained genetic algorithm within the wavelets coefficients data. In the present inventive systems and methods, the two or more groups may include any refinery product or intermediate stream that may be transported by pipeline as well as mixtures of these products or intermediate streams. In certain embodiments, such mixtures may be classified as "intermix/transmix" by the trained genetic algorithm.

In certain embodiments, the data generated by the automated analyzer is utilized to predict the fouling propensity of a given sample of crude oil (or any liquid or gaseous product that can be derived from a crude oil through commercial refinery processes) requires crude assay information that can only be obtained by analytical assays that take six hours or more to complete. This greatly hampers the rapid identification of crude oil samples that are capable of fouling process equipment in a commercial refinery setting, leading to potentially increased operating costs.

To demonstrate certain embodiments, we developed processes that could rapidly identify the fouling propensity of a given crude oil sample by developing a model that is based upon near-infrared (NIR) spectral data, nuclear magnetic resonance (NMR) spectra, or both. The inventive processes and systems disclosed herein successfully distinguish a specific property of a crude oil sample (i.e., the fouling propensity) based solely upon analysis of specific features obtained from this spectral data. This represents a significant advance in rapidly identifying favorable crudes for use in a commercial petroleum refinery setting.

Certain embodiments of the inventive process utilize spectral data obtained from at least one of near infrared spectroscopy (NIR) and nuclear magnetic resonance spectroscopy (NMR) because these techniques are capable of being used to capture "chemical fingerprints" of crude oil samples that can be correlated with the fouling tendencies of each sample. More specifically, NIR spectroscopy provides excited vibrational data while NMR spectroscopy provides data on magnetic field induced molecular chemical shifts that are indicative of the overall molecular composition of each crude oil sample. When utilized together, these two types of data may help to more easily identify informative spectral differences between fouling and non-fouling crude oil samples. However, while this distinguishing information is buried within the spectra, it has been impossible to identify these differences solely via conventional attempts to interpret the spectral data. Although NIR and NMR have the unique advantages of capturing significant identifying information about a crude oil sample (when compared to data obtained by other analytical assays), the complexity and subtlety of these spectral signals has been an obstacle to effectively interpreting differences between crude oil samples.

In addition, certain embodiments of the present inventive process are the first to successfully combine NIR spectral data and NMR spectral data to train a genetic algorithm to classify samples of crude oil via the judicious application of wavelet theory to transform the spectral data to wavelet coefficients data that is then utilized to train a genetic algorithm. The selection of an unexpectedly advantageous mother wavelet and concatenation of very subtle but informative selected spectral features enabled the success of the present inventive methodology.

The inventive process and system in part comprises mathematical transformation of the spectral data to wavelets to enhance subtle but informative features in the data. According to wavelet theory, a discrete signal such as can be decomposed into "approximation" and "detail" components. Wavelet packet transform (WPT) was applied to de-noise and de-convolute spectra of crude oil samples by decomposing each spectrum (comprising spectral data) into wavelet coefficients that represent the constituent frequencies of that spectrum.

Wavelets offer a different approach to removal of noise from multivariate data than other techniques such as Savitzky-Golay filtering or the fast Fourier transform. Wavelets can often enhance subtle but significant spectral features to increase the general discrimination power of the modeling approach. Using wavelets, a new set of basis vectors is developed in a new pattern space that takes advantage of the local characteristics of the data. These new basis vectors are capable of better conveying the information present in the data than axes that are defined by the original measurement variables.

In certain embodiments of the inventive process, spectral signals were "decomposed" by passing each spectrum through low-pass and high-pass scaling filters to produce a low-frequency "detail" coefficient dataset and a high-frequency "approximation" coefficient dataset. The approximation coefficients correspond to the "low-frequency signal" data in the spectra, while the detail coefficients usually correspond to the "noisy signal" portion of the data. The process of decomposition was continued with different scales of the wavelet filter pair in a step-by-step fashion to separate the noisy components from the signal until the necessary level of signal decomposition was achieved. We have found that wavelet coefficients are especially important and preferred (versus raw spectral data) in modeling fouling propensity because the nature of the basis vectors used to characterize the data are conducive to a variety of approaches for improving the quality of the input data for training. In particular, we unexpectedly found that decomposition of the data using the Symlet6 mother wavelet unexpectedly enabled a genetic algorithm to distinguish spectral features in the resulting wavelet coefficients data that enabled classification of crude oil samples into two groups based upon their fouling propensity.

Figure 10:
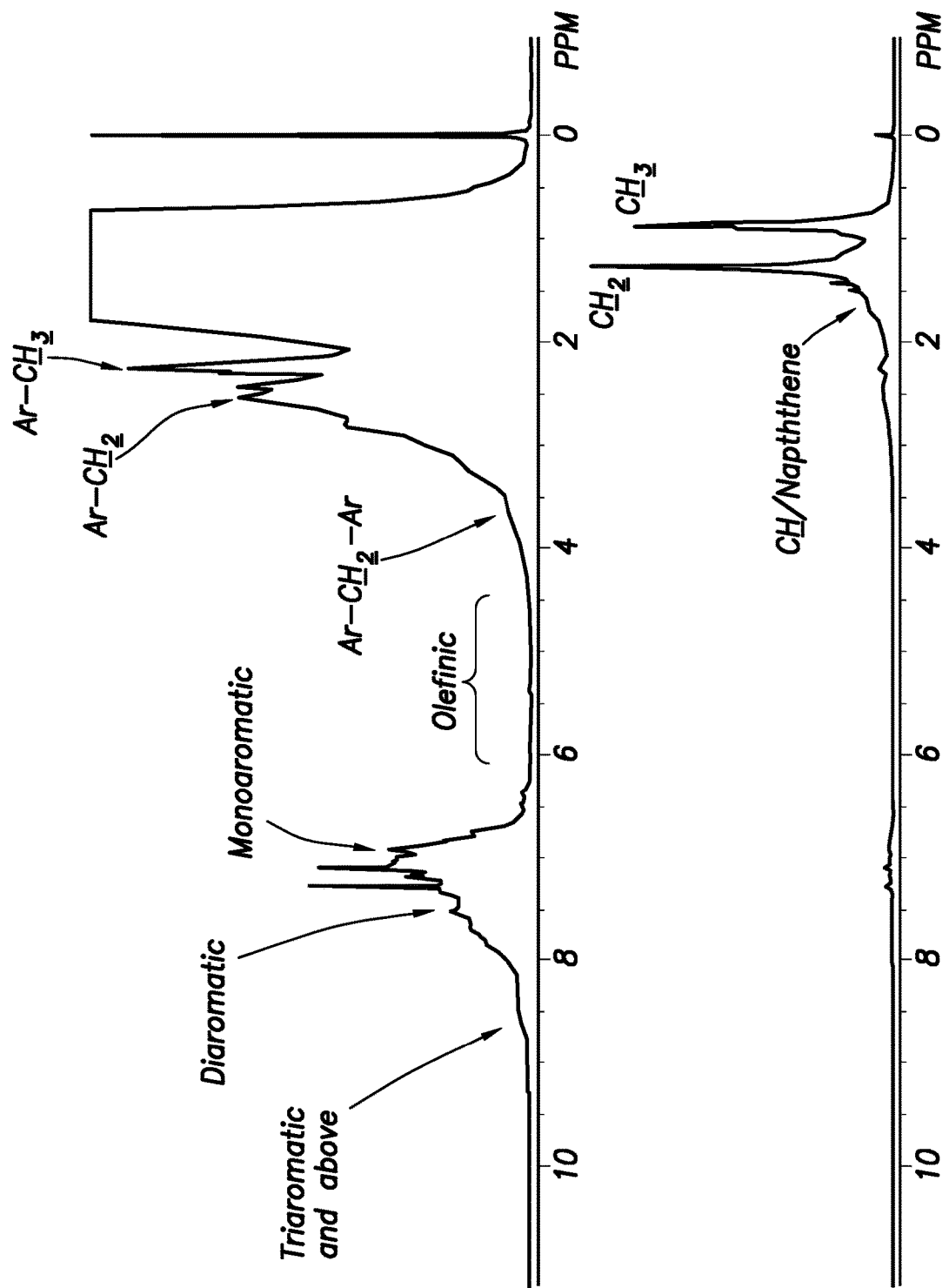
FIG. 10 depicts a typical NMR spectrum for a sample comprising crude oil (lower panel), and a view of the same spectrum with the Y-axis amplified (upper panel).

As mentioned, certain embodiments comprise first obtaining spectral information for a given sample comprising crude oil. NIR spectral data, NMR spectral data, or both are obtained by the automated analyzer. The presence of numerous signals in the NMR spectrum is beneficial because those signals provide a type of fingerprint of the crude oil sample that provides spectral features that allow discrimination between oil samples capable of fouling versus those that are not. FIG. 10 depicts a typical NMR spectrum of a sample comprising crude oil, which includes a large number of signals attributed to diverse hydrocarbon types and complex molecular structures. The assignments of chemical shift regions to the corresponding molecular structural types are shown in Table 1 (below).

TABLE 1

Assignments of 1H NMR chemical shifts.

| Chemical Shift Region (ppm) | Assignments |
|---|---|
| 0.2-1.0 | aliphatic $CH_3$ |
| 1.0-1.4 | aliphatic $CH_2$ |
| 1.4-2.0 | naphthenics or CH in isoparaffins |
| 2.0-2.4 | $CH_3$ alpha to aromatics |
| 2.4-3.5 | $CH_2$ or CH alpha to aromatics |
| 3.5-4.5 | bridged $CH_2$ in fluorene types |
| 4.5-6.2 | olefins or diolefins |
| 6.2-7.4 | single-ring aromatics |
| 7.4-8.3 | diaromatics |
| 8.3-10.0 | 3-ring polyaromatics and above |

The region spanning 0.2-1.0 ppm corresponds to aliphatic $CH_3$, region 1.0-1.4 ppm is assigned to aliphatic $CH_2$, region 1.4-2.0 ppm is assigned to naphthenics or CH in isoparaffins, region 2.0-2.4 ppm is attributed to $CH_3$ alpha to aromatics, region 2.4-3.5 ppm corresponds to $CH_2$ or CH alpha to aromatics, region 3.5-4.5 ppm is assigned to bridged $CH_2$ in fluorenes, region 4.5-6.2 ppm is due to olefins or diolefins, region 6.2-7.4 ppm is attributed to single-ring aromatics, region 7.4-8.3 ppm corresponds to diaromatics, and region 8.3-10.0 ppm is assigned to polyaromatics with three rings and above.

Certain embodiments may comprise acquiring $^{13}C$ NMR data rather than $^1H$ NMR data. While the specifics may differ with regards to chemical shifts, the general concept is identical to the utilization of $^1H$ NMR data in conjunction with the present inventive processes.

One having average skill in the area of NMR spectroscopy would be familiar with the implementation of $^{13}C$ NMR in place of $^1H$ NMR data, and thus, there is no need to disclose this in greater detail herein.

Certain embodiments comprise obtaining near-infrared spectral data for a sample comprising crude oil. Near-infrared spectral data is typically obtained for wavelengths in the range from 3000 to 6000 cm'. Each NIR spectrum is represented by a finite number of wavelet coefficients that typically varies from 50-5000 using a member of the Symlet mother wavelet family to perform multiple rounds of data decomposition to denoise and deconvolute the spectra. In certain embodiments, the NIR spectrum may be represented by 300-3000 wavelet coefficients, (e.g., 1333). It is important to note that the selection of alternative mother wavelets other than the Symlet for decomposition of the NIR spectral data results in a profoundly decreased ability for a pattern recognition genetic algorithm to classify crude oil samples according to fouling propensity.

Wavelet packet transform is applied to de-noise and de-convolute spectra of crude oil samples by decomposing each spectrum into coefficients (wavelet coefficients) that represent the sample's constituent frequencies. According to wavelet theory, a discrete signal such as an NIR spectrum can be decomposed into "approximation" and "detail" components. Wavelets will often enhance subtle but significant spectral features to increase the general discrimination power of the modeling approach.

Wavelets offer a different approach to removing noise from multivariate data than Savitzky-Golay filtering or the fast Fourier transform. Using wavelets, a new set of basis vectors are developed that take advantage of the local characteristics of the data, and these vectors convey the information present in the data better than axes defined by the original measurement variables (wavelength). Wavelet coefficients provide the coordinates of the samples in this new pattern space. The mother wavelet selected to develop the new basis set is the one that best matches the attributes of the data. This gets around the problem that occurs when an interfering source of variation in the data is correlated to information about the class membership of the samples (for example, fouling and/or non-fouling) as a result of the design of the study or because of accidental correlations between signal and noise.

Figure 11:
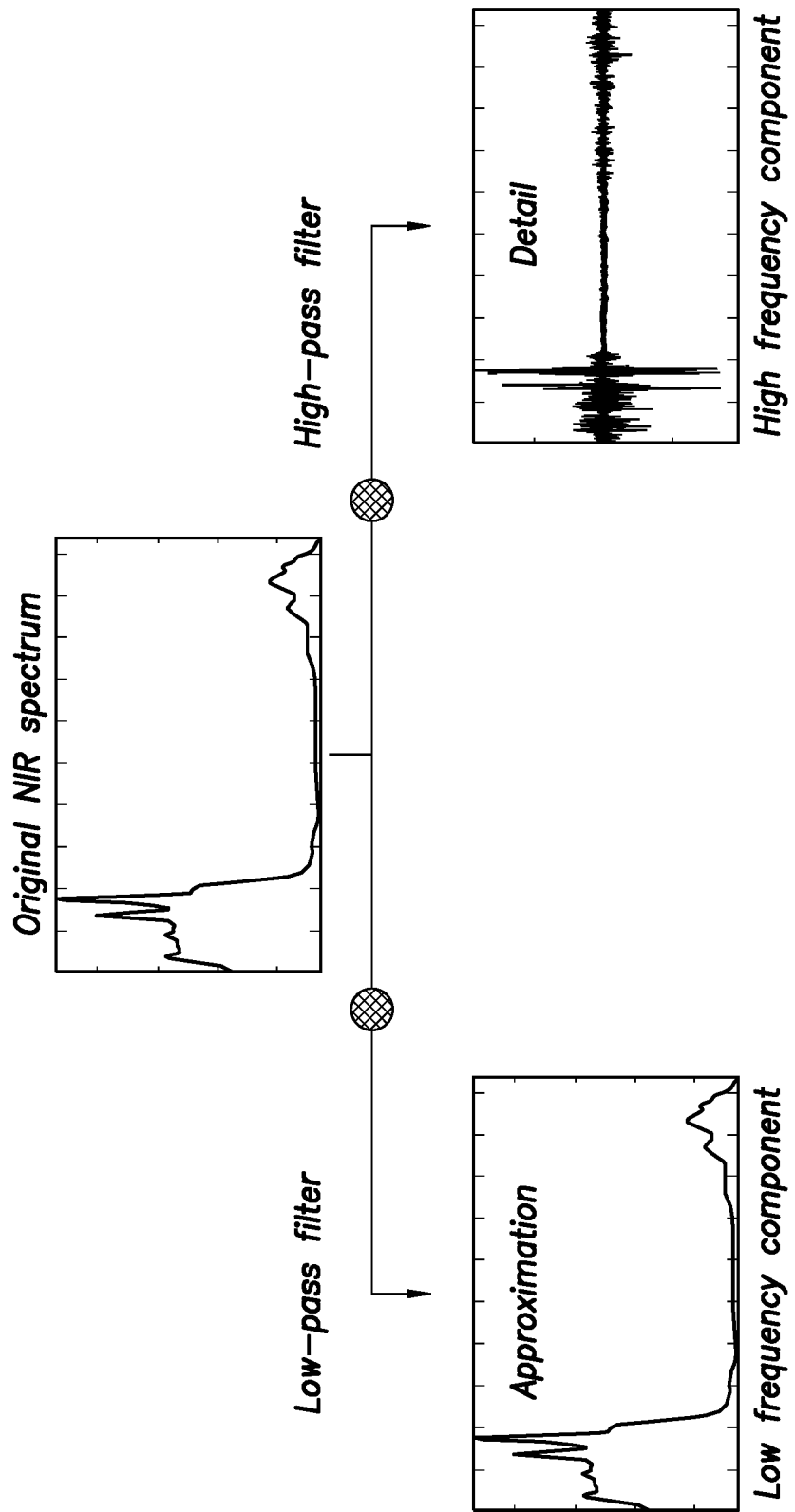
FIG. 11 depicts a diagram demonstrating the decomposition of spectral data according to wavelet theory.
Figure 12:
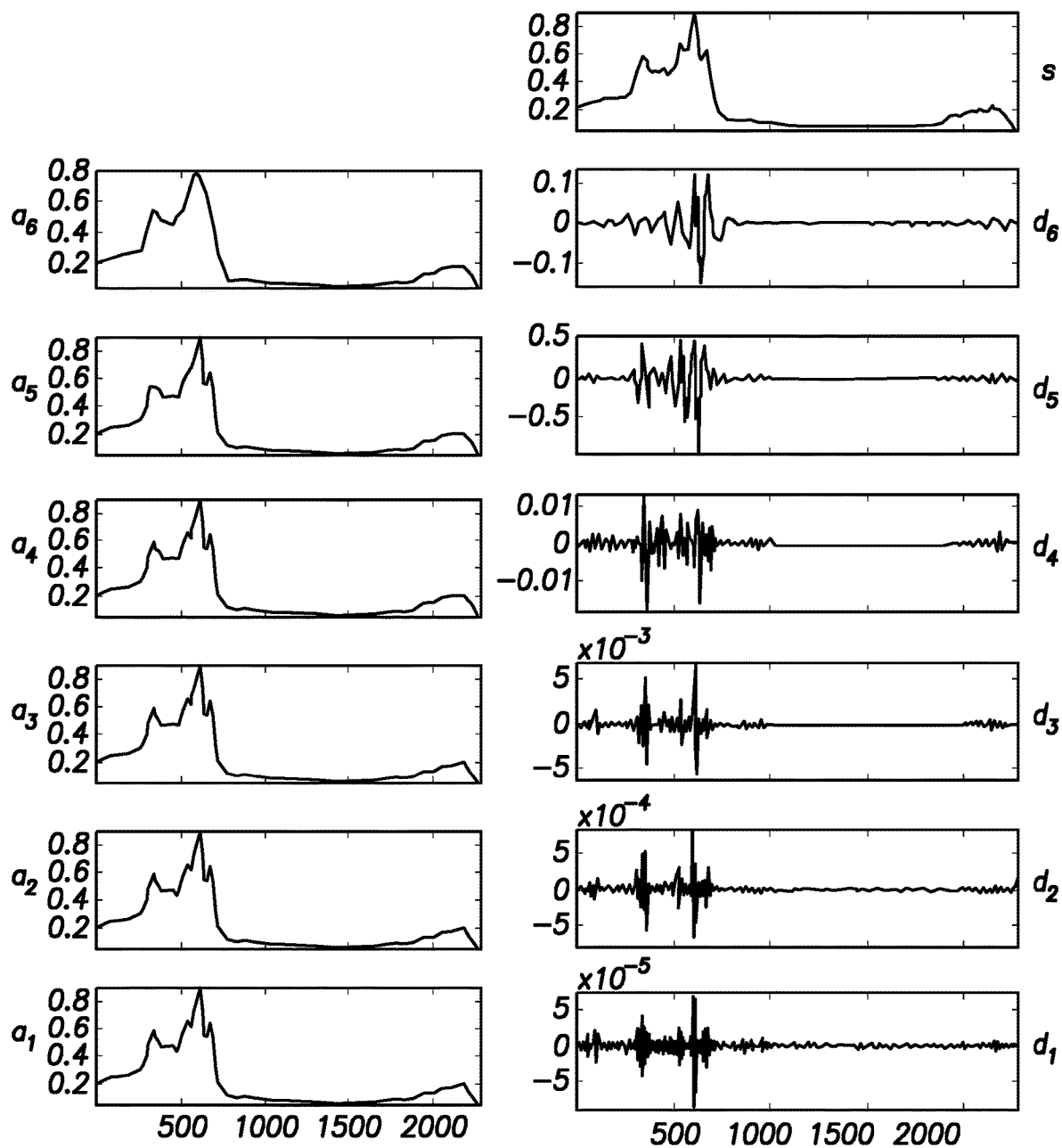
FIG. 12 depicts progressive decomposition of NIR spectral data to produce approximation (a) and detail (d) coefficients data from the first to sixth levels.

Using wavelets, spectral data is decomposed by passing through two scaling filters: a high-pass filter and a low-pass filter (FIG. 11). The low-pass filter allows only the low-frequency component of the signal to be measured as a set of wavelet coefficients, which is called the "approximation." The high-pass filter measures the high-frequency coefficient set, which is called the "detail." The detail coefficients usually correspond to the noisy part of the data. This process of decomposition is continued with different scales of the wavelet filter pair in a step-by-step fashion to separate the noisy components from the signal until the necessary level of signal decomposition has been achieved. FIG. 12 demonstrates an exemplary result utilizing this technique on NIR spectral data (displayed in transmittance mode) obtained from a sample comprising crude oil. FIG. 12 displays the results of wavelet decomposition of the spectral data performed up to the sixth level for the approximation ($a_1$-$a_6$) and detail ($d_1$-$d_6$) components, while "s" indicates the original NIR spectrum.

Wavelet coefficients are especially important and are preferred to raw spectral data for modeling fouling propensity because the nature of the basis vectors used to characterize the data is conducive to a variety of approaches for improving the quality of the data that is used for model training. The wavelet coefficients obtained from each spectrum are organized as a data vector, and each coefficient is auto-scaled. A mother wavelet is selected to develop the new basis set, and historically, certain classes of mother wavelet have been commonly utilized that are considered to be the most effective at extracting distinguishing class information from spectral data. Selecting a mother wavelet to use as a "reference point" helps solve the problem that occurs when an interfering source of variation in the data is correlated to information about the class membership of the samples (e.g. fouling and/or non-fouling) as a result of the design of the study or because of accidental correlations between signal and noise.

During development of certain embodiments of the process it was unexpectedly discovered that the Symlet family of mother wavelets was particularly well-suited to deconvolute and denoise both NIR and NMR spectral data. In fact, applying the Symlet mother wavelet dramatically increased the power of the inventive process to discriminate between fouling and non-fouling crude oil samples. Symlet wavelets are a family of mother wavelets that are modified versions of Daubechies wavelets that are characterized by increased symmetry. Daubechies wavelets are a family of orthogonal wavelets defining a discrete wavelet transform and are characterized by a maximal number of vanishing moments for some given support. With each wavelet type of this class, there is a scaling function (called the/ix/her wavelet) which generates an orthogonal multiresolution analysis. Applying the Symlet mother wavelet to analysis and classification of the NIR and NMR spectral data is highly unconventional because conventional practice is to perform mathematical deconvolution of spectral data that is characterized by broad-band signals (e.g., near-infrared spectra) using the "Haar" family of mother wavelets. Conventional wisdom asserts that the Symlet family of mother wavelets should only be applied to decomposition of spectral signals that are characterized by numerous sharp peaks (such as mid-infrared spectral data, or chromatographic data) and that the "Haar" family of mother wavelets is far better-suited for decomposition of NIR or NMR spectral data, which typically do not comprise numerous sharp peaks.

Certain embodiments utilize the Symlet4 mother wavelet, while certain alternative embodiments utilize the Symlet6 mother wavelet. The inventive process may apply a Symlet mother wavelet at the third or greater level of decomposition; alternatively, the fourth level of decomposition or greater; alternatively, the fifth level of decomposition. The choice of the Symlet mother wavelet at the third (alternatively, fourth) level of decomposition was found to unexpectedly and fortuitously enhance the rather subtle but informative spectral features in the spectra. This resulted in an improved power of the inventive process to discriminate between fouling and non-fouling crude oil samples.

Certain embodiments of the inventive present process generally comprise training a genetic algorithm or utilizing support vector machines to distinguish between wavelet coefficients data obtained for samples comprising crude oil that are either capable of fouling refinery process equipment versus those that are not. A genetic algorithm is a search heuristic that is inspired by Charles Darwin's theory of natural evolution. This algorithm reflects the process of natural selection where the fittest individuals are selected for reproduction in order to produce offspring of the next generation. The process of natural selection starts with the selection of fittest individuals from a population. They produce offspring which inherit the characteristics of the parents and will be added to the next generation. If parents have better fitness, their offspring will be better than parents and have a better chance at surviving. This process is iterative and eventually results in a generation with the fittest individuals identified. The specifics of training and applying genetic algorithms is familiar to those having experience in the field of data analysis, and thus a more detailed explanation is not provided here.

In certain embodiments of the present inventive process, a genetic algorithm for pattern-recognition analysis is trained to identify distinguishing features within wavelet coefficients data derived from aliquots comprising crude oil, thereby allowing the trained genetic algorithm to classify crude oil samples into two groups depending on their characteristic capacity to foul refinery equipment and processes, or not. In general, a non-fouling crude petroleum sample is characterized by a fouling thermal resistance of less than 0.002 hr-ft$^2$-° F./British Thermal Unit (BTU), while a fouling crude petroleum sample is characterized by a fouling thermal resistance of at least 0.002 hr-ft$^2$-° F./BTU Even in challenging trials, the present inventive method correctly classified a variety of crude oil samples as either fouling or non-fouling via the identification of selected discriminating features that were developed from wavelet coefficients and identified by a pattern-recognition genetic algorithm.

In certain embodiments, the genetic algorithm is trained using spectral data obtained from five or more aliquots of crude oil having varying fouling thermal resistance characteristics and that are preferably of distinct geologic origin. Certainly, a larger number of distinct aliquots of crude oil is preferred and will result in a trained genetic algorithm that can better discriminate between fouling and non-fouling samples. In certain embodiments, training the genetic algorithm to distinguish between fouling and non-fouling crude petroleum samples may utilize the spectral data obtained from at least 20, at least 35, or at least 50 distinct aliquots of crude oil. The pattern-recognition genetic algorithm may utilize both supervised learning and unsupervised learning to identify the wavelet coefficients data that corresponds to features (from NIR data) and/or chemical shifts (from NMR data) that facilitate the ability of the genetic algorithm to classify each crude oil sample as either fouling or non-fouling. In embodiments that comprise supervised learning, manual curation to exclude certain data features is performed based upon the probability that such features may have resulted from areas of the spectral data with a low signal to noise ratio. The result of such manual curation is a subset of features (often the two or three largest principal components of the data) that is utilized by the trained genetic algorithm to classify each sample comprising crude oil. Pattern-recognition by the genetic algorithm of spectral feature differences representing the principal components in crude oil samples maximizes the variance between groups (i.e., fouling and non-fouling samples), which also maximizes the percentage of data utilized by the pattern recognition genetic algorithm to classify each sample that is derived from spectral differences between the groups. A principal-component plot that shows separation of the samples into two groups can be generated using only a curated subset of spectral features that provide the most information about the differences between the crude oil samples, simplifying classification along fouling lines. This fitness criterion dramatically reduces the size of the search space because it limits the classification search to a small number of spectral features within the wavelet coefficients data that are capable of distinguishing unknown samples comprising crude oil into one of the two classes.

Further, as the pattern-recognition genetic algorithm trains, it focuses on those samples that are difficult to classify by boosting the relative importance of distinguishing spectral features associated with those samples. Over time, the genetic algorithm learns in a manner similar to how a neural network learns. The pattern-recognition genetic algorithm integrates aspects of artificial intelligence and evolutionary computations to yield the trained genetic algorithm of the present inventive processes and systems.

Certain embodiments utilize support vector machines rather than a trained genetic algorithm to classify crude oil samples as either fouling or non-fouling. Support vector machines (SVM) and neural networks are examples of non-parametric discriminants that operate by attempting to divide a data space into distinct regions. For a binary classifier, the data space is divided into two regions. Samples that share a common property will be found on one side of the decision surface, while those samples classified in the second category will be found on the other side. The present process efficiently divides the data space into two regions: crude oil samples that are characterized as either "fouling" or "non-fouling".

SVM can be used to address classification and regression problems. In classification context, they generate linear boundaries between object groups in a transformed space of the x-variables, which are usually of much higher dimension than the original x-space. The idea of the transformed higher dimensional space is to make groups linearly separable. These class boundaries are constructed in order to maximize the margin between the groups.

Figure 13:
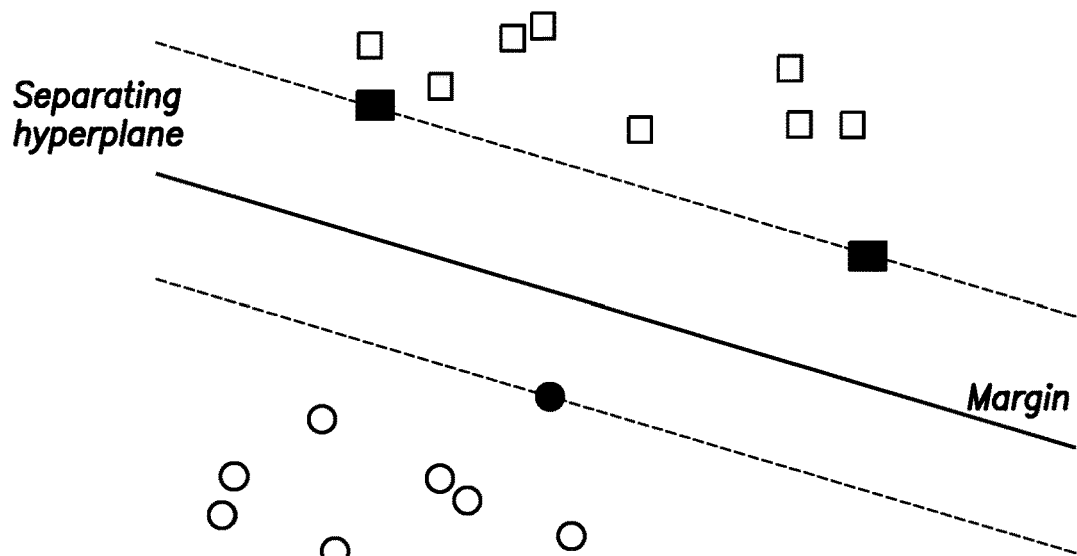
FIG. 13 depicts a plot of samples representing two classes separated by a separating hyperplane.

SVM identifies decision surfaces or hyperplanes that establish the widest margin to discriminate between samples belonging to different classes in a data set. An example hyperplane is shown in FIG. 13, with samples representing one class (circles) on one side of the dividing hyperplane and samples representing a second class on the opposite side of the separating hyperplane. The algorithm uses only some samples in the data set, which are known as support vectors. The input data are mapped from the original measurement space to a higher-dimensional space using kernel functions to simplify the classification problem. There are a variety of kernel functions, including linear kernels for linear hyperplanes as well as polynomial, Gaussian, and sigmoidal kernels for nonlinear decision surfaces. Kernel functions simplify the classification problem by allowing direct computation of the dot product of the weight vector, which defines the distance between the hyperplane and each support vector in the original measurement space. For a linearly separable data set, there will be a large number of linear hyperplanes that can be developed to separate samples into their respective classes. The hyperplane best able to generalize the data (i.e., accurately classify both the training and test sets) is the one with the widest margin. For data sets that are not linearly separable, a nonlinear decision surface will be used (e.g. separating fouling from non-fouling crude oil samples). The kernel function that yields the best classification of the samples is selected for discriminant development. When a classification rule is being developed for a non-separable data set, the optimization problem is reformulated to allow for samples, but as few as possible, to be present in the margin. SVM have some unique advantages. They have good generalization ability because the optimization problem is less prone to over-fitting when the appropriate kernel functions are used. This is because there are fewer model parameters to compute from the data. In addition, SVM are easier to train when compared with conventional methods.

Figure 14:
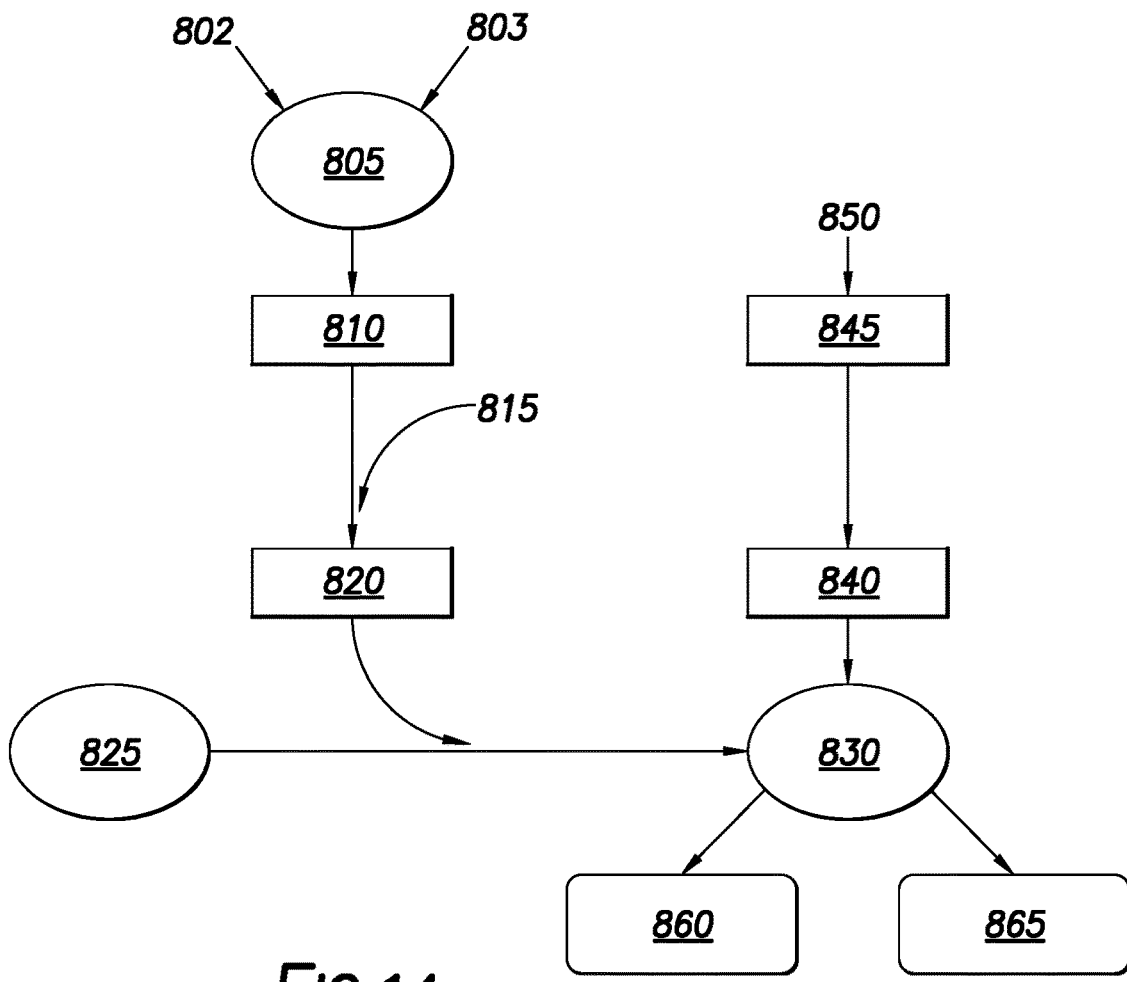
FIG. 14 is a simplified diagram depicting an embodiment of the present inventive process and system.

An embodiment of the inventive process and system that trains a GA and then utilizes the trained GA is illustrated by the flow diagram of FIG. 14. In general terms, the embodiment comprises training a genetic algorithm to recognize subtle collective differences within data obtained from two groups, a first group comprising aliquots of non-fouling crude oil that are each characterized by a fouling thermal resistance of less than 0.002 hr-ft$^2$-° F./BTU and a second group comprising aliquots of crude oil that are each characterized by a fouling thermal resistance of at least 0.002 hr-ft$^2$-° F./BTU and are capable of causing fouling in petroleum refinery processes and equipment.

The training wavelet coefficients data obtained from aliquots of the first group are collectively compared to the training wavelet coefficients data obtained from aliquots of the second group by the genetic algorithm, wherein the genetic algorithm performs an iterative process that eventually distinguishes spectral features that differ between the first group (viewed collectively) and the second group, thereby producing a trained genetic algorithm. The trained genetic algorithm is then capable of quickly classifying a sample of a crude oil feed stock (having an unknown fouling thermal resistance) as a member of the first or the second group.

In the embodiment shown in FIG. 14, multiple aliquots comprising crude petroleum that are collectively referred to as the first group 802 and multiple aliquots comprising crude petroleum that are collectively referred to as the second group 803 are analyzed by a spectral method 805 comprising at least one of NIR and NMR to produce spectral data 810, where the spectral data obtained for each aliquot by spectral method 805 comprises multiple distinct digitized data points. Each of the first group 802 and the second group 803, respectively, comprise at least five aliquots, where each aliquot is preferably of distinct geologic origin from others within the group and in the case of the second group, each aliquot is characterized by a different fouling thermal resistance of at least 0.002 hr-ft$^2$-° F./BTU.

The spectral data 810 for each aliquot is transformed to training wavelet coefficients data 720 according to wavelet theory by processing the data using a mother wavelet 815 that comprises a member of the Symlet family of mother wavelets. In certain embodiments, a member of the Symlet mother wavelet family that is selected from the Symelet4 and Symlet6 mother wavelets. The mother wavelet 815 is utilized to decompose the spectral data 810 to the third level of decomposition or greater to produce training wavelet coefficients data 820. Commercially available computer software (for example, but not limited to, MATLAB®) may be employed to facilitate the iterative decomposition process, but such software is not essential in order to practice the inventive process as described herein.

The embodiment trains a genetic algorithm, which comprises presenting an untrained genetic algorithm 825 that designed to perform data pattern recognition with the training wavelet coefficients data 820 obtained from each of the multiple aliquots comprising the first group 802 and the second group 803, respectively. While training, the untrained genetic algorithm 825 recognizes subtle patterns, or spectral features that are located within the training wavelet coefficients data 820 to produce a trained genetic algorithm 830 that utilizes a the potential differentiating data features to classify a given sample comprising crude oil as either non-fouling or fouling.

The trained genetic algorithm 830 is operable to recognize differentiating data features within sample wavelets coefficients data 840 that is derived from the sample NIR and/or NMR spectral data 845 of an uncharacterized sample 850 comprising crude oil. The trained genetic algorithm 830 then classifies the uncharacterized sample 850 comprising crude oil as a either first group feed stock 860 or a second group feed stock 865 wherein the first group feed stock 860 comprises a non-fouling crude oil sample characterized by a fouling thermal resistance of less than 0.002 hr-ft$^2$-° F./BTU and the second group feed stock 865 comprises a fouling crude oil test sample characterized by a fouling thermal resistance of at least 0.002 hr-ft$^2$-° F./BTU. The uncharacterized sample 850 is analyzed by NIR and/or NMR in a similar (or identical) way as was descried for the multiple aliquots comprising the first group 802 and the second group 803 to acquire the sample NIR and/or NMR spectral data 845. The sample NIR and/or NMR spectral data 845 is converted to sample wavelets coefficients data 840 that is then presented to the trained genetic algorithm 835. The trained genetic algorithm 835 recognizes differentiating data features within the sample wavelets coefficients data 840, which enables the trained genetic algorithm 835 to classify the uncharacterized sample 850 as a member of either the first group 860 or the second group 865.

Certain embodiments comprise manually curating potential differentiating features in the wavelets coefficients data that are identified by the genetic algorithm. This eliminates potential differentiating features with the highest probability of being a false positive (i.e., derived from a region of the spectral data that is characterized by a low signal to noise ratio). A second embodiment of the inventive process and system that includes manual curation of the data is illustrated by the flow diagram of FIG. 15.

The embodiment comprises training a pattern-recognition genetic algorithm to recognize subtle collective differences within data obtained from two groups, a first group comprising aliquots of non-fouling crude oil that are each characterized by a fouling thermal resistance of less than 0.002 hr-ft$^2$-° F./BTU and a second group comprising aliquots of crude oil that are each characterized by a fouling thermal resistance of at least 0.002 hr-ft$^2$-° F./BTU and typically capable of causing fouling in petroleum refinery processes and equipment.

Similar to the first embodiment, the training wavelet coefficients data obtained from aliquots of the first group are collectively compared to the training wavelet coefficients data obtained from aliquots of the second group by the genetic algorithm, wherein the genetic algorithm performs an iterative process that eventually distinguishes spectral features that differ between the first group (viewed collectively) and the second group, thereby producing a trained genetic algorithm. The trained genetic algorithm is then capable of quickly classifying a sample of a crude oil feed stock (having an unknown fouling thermal resistance) as a member of the first or the second group.

Figure 15:
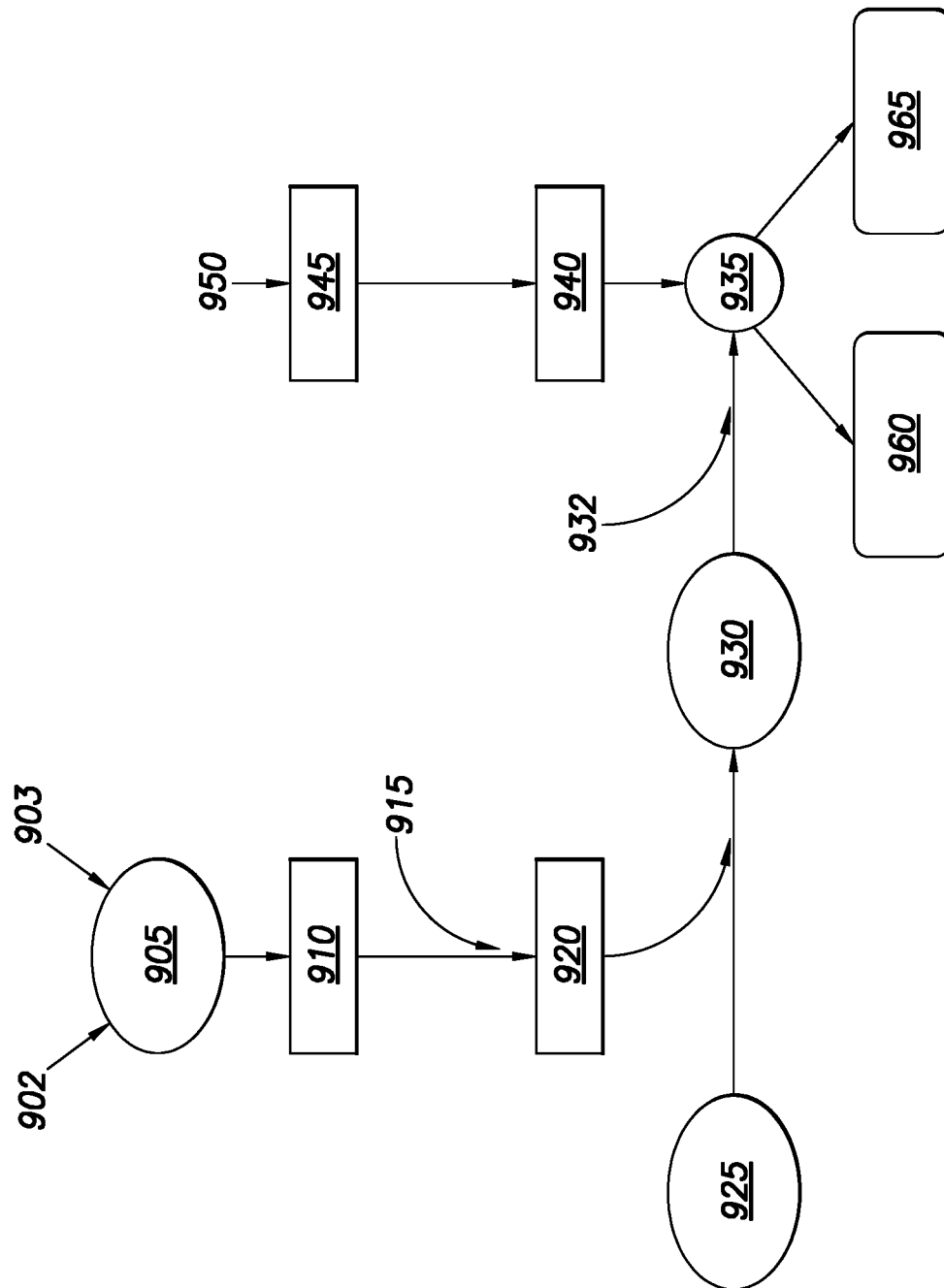
FIG. 15 is a simplified diagram depicting an embodiment of the present inventive process and system.

In the embodiment shown in FIG. 15, multiple aliquots comprising crude petroleum that are collectively referred to as the first group 902 and multiple aliquots comprising crude petroleum that are collectively referred to as the second group 903 are analyzed by a spectral method 905 comprising at least one of NIR and NMR to produce spectral data 910, where the spectral data obtained for each aliquot by spectral method 905 comprises multiple distinct digitized data points. Each of the first group 902 and the second group 903, respectively, comprise at least five aliquots, where each aliquot is preferably of distinct geologic origin from others within the group and in the case of the second group, each aliquot is characterized by a different fouling thermal resistance of 0.002 hr-ft$^2$-° F./BTU or more.

The spectral data 910 for each aliquot is transformed to training wavelet coefficients data 820 according to wavelet theory by processing the data using a mother wavelet 915 that comprises a member of the Symlet family of mother wavelets. In certain embodiments, a member of the Symlet mother wavelet family that is selected from the Symelet4 and Symlet6 mother wavelets. The mother wavelet 915 is utilized to decompose the spectral data 910 to the third level of decomposition or greater to produce training wavelet coefficients data 920. Commercially available computer software (for example, but not limited to, MATLAB®) may be employed to facilitate the iterative decomposition process, but such software is not essential in order to practice the inventive process as described herein.

The embodiment trains a genetic algorithm, which comprises presenting an untrained genetic algorithm 925 that designed to perform data pattern recognition with the training wavelet coefficients data 920 obtained from each of the multiple aliquots comprising the first group 902 and the second group 903, respectively. While training, the untrained genetic algorithm 925 recognizes subtle patterns, or spectral features that are located within the training wavelet coefficients data 920 to produce a trained genetic algorithm intermediate 930. In the embodiment depicted in FIG. 15, potential differentiating data features that are recognized by the untrained genetic algorithm 925 to produce the trained genetic algorithm intermediate 930 are then subjected to manual curation 932 to produce a trained genetic algorithm 935 that utilizes a curated subset of the potential differentiating data features to classify a given sample comprising crude oil as either non-fouling or fouling. Manual curation 932 of potential differentiating data features comprises eliminating from consideration any potential differentiating data features recognized by the untrained trained genetic algorithm 925 that are deemed by either a process operator or an automated curation process to have a high probability of contributing to an inaccurate classification. Potential differentiating data features most likely to be subject to manual curation typically are in a region of the spectral data where the data is typically characterized by a low signal to noise ratio.

The trained genetic algorithm 935 is characterized by a curated subset of differentiating data features, which makes the trained genetic algorithm 935 operable to recognize differentiating data features within sample wavelets coefficients data 940 that is derived from the NIR and/or NMR spectral data 945 of an uncharacterized sample 950 comprising crude oil. The trained genetic algorithm 935 then classifies the uncharacterized sample 950 comprising crude oil as a either first group feed stock 960 or a second group feed stock 965 wherein a first group feed stock 960 comprises a non-fouling crude oil sample characterized by a fouling thermal resistance of less than 0.002 hr-ft$^2$-° F./BTU and a second group feed stock 965 comprises a fouling crude oil test sample characterized by a fouling thermal resistance of at least 0.002 hr-ft$^2$-° F./BTU.

The uncharacterized sample 950 is analyzed by NIR and/or NMR in a similar (or identical) way as was descried for the multiple aliquots comprising the first group 902 and the second group 903 to acquire the NIR and/or NMR spectral data 945. The NIR and/or NMR spectral data 945 is converted to sample wavelets coefficients data 940 that is then presented to the trained genetic algorithm 935. The trained genetic algorithm 935 recognizes differentiating data features within the sample wavelets coefficients data 940, which enables the trained genetic algorithm 935 to classify the uncharacterized sample 950 as a member of either the first group 960 or the second group 965.

The following examples of certain embodiments of the invention are given. Each example is intended to illustrate a specific embodiment, but the scope of the invention is not intended to be limited to the embodiments specifically disclosed. Rather, the scope is intended to be as broad as is supported by the complete disclosure and the appending claims.

Example 1

As a first step toward training a genetic algorithm to distinguish those crude oils having the potential to foul refinery processes, 63 crude oils samples of distinct geologic origin were obtained and their fouling propensity was determined in a conventional manner using a conventional Hot Liquid Process Simulator (HPLS), prior to analyzing the samples by either near-infrared spectroscopy (NIR) or nuclear magnetic resonance spectroscopy (NMR). While an HPLS apparatus may be utilized to measure fouling thermal resistance of crude samples utilized with the present inventive processes, other conventional laboratory tests may also be utilized to measure fouling thermal resistance.

Figure 16:
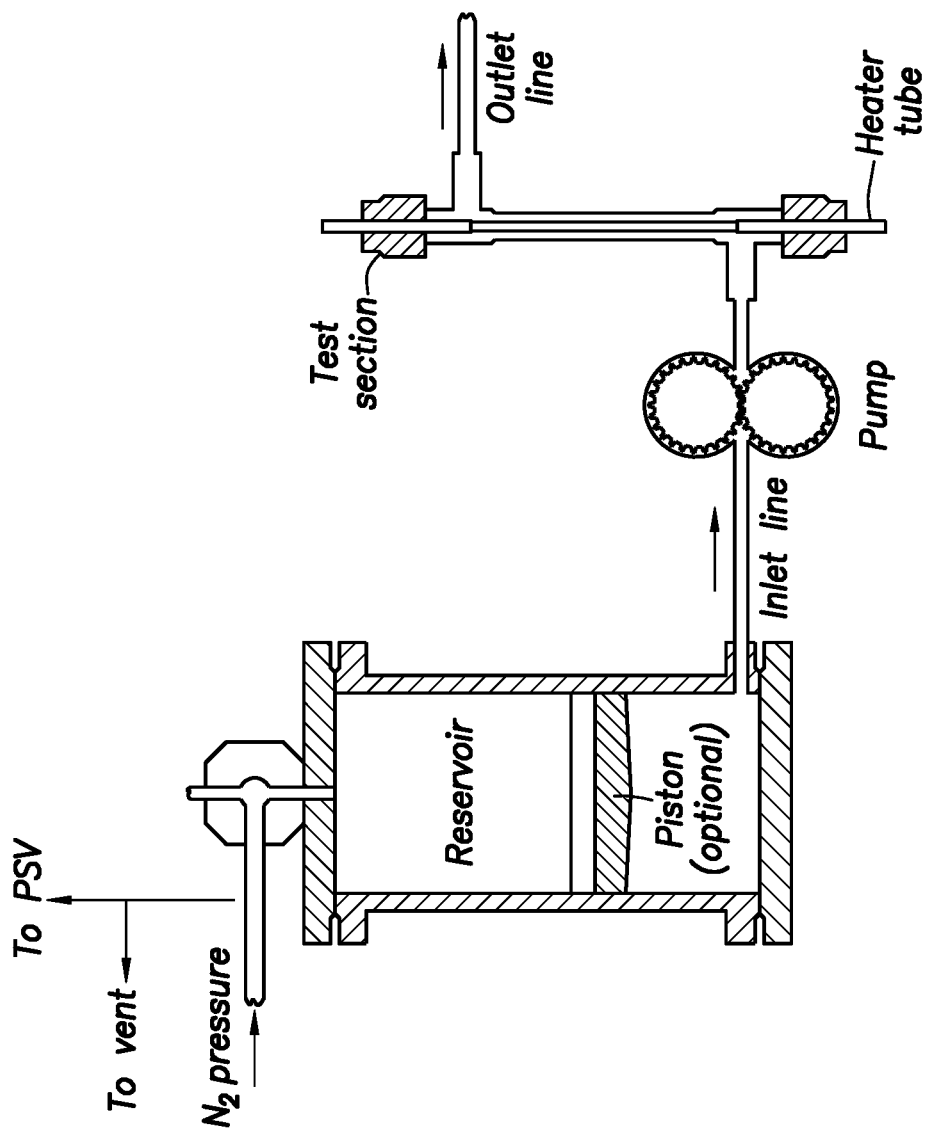
FIG. 16 depicts a simplified diagram of a hot liquid process simulator apparatus.

The general operational layout of a HPLS is diagramed in FIG. 16. The HPLS pumps a test liquid upward through an annular test section that contains a heated rod made of carbon steel. The heated rod is hollow, with an internally mounted control thermocouple, and the rod is electrically heated to maintain constant temperature. The following test conditions were chosen:
Rod temperature: 698° F. (370° C.)
Rod Metallurgy: Carbon Steel
Liquid feed line and pump temperature: 22° C.
Flow rate: 1 mL/min (no recirculation)
Line pressure: 500 psig As foulants accumulate on the rod, they insulate the rod and reduce the rate of heat transfer to the liquid, thereby causing a decrease over time of the temperature of the test liquid measured at the outlet of the test chamber containing the heated rod. The results are expressed as fouling thermal resistance (FTR) per unit of time (set at 1 hr) per sq. ft. where FTR is equal to the inverse of the heat transfer coefficient (or, 1/U). Thus, FTR=1/U=A×ΔT÷Q, where
Q=heater rod power
U=heat transfer coefficient
A=surface area of the heater rod
ΔT=change in temperature of the rod=$T_{ROD}$−($T_{INLET}$+$T_{OUTLET}$)/2

Using the HPLS, FTR values were determined for the 63 different aliquots comprising crude oil feed stocks of distinct geologic origin and obtained from different regions around the world. The resulting FTR values ranged from 0.000 hr-ft$^2$-° F./BTU to 0.00616 hr-ft$^2$-° F./BTU. A crude oil sample characterized by a FTR value below 0.002 hr-ft$^2$-° F./BTU (as measured by the HPLS) were classified as "non-fouling" (Group 1), while a crude oil sample with a fouling thermal resistance that met or exceeded a value of 0.002 hr-ft$^2$-° F./BTU or above was classified as "fouling". All units of thermal fouling resistance in the present disclosure are as measured by the HPLS method, which may not necessarily coincide with actual fouling thermal resistance.

Example 2

From the 63 samples comprising crude oil that were characterized for fouling characteristics in Example 1, approximately 30 aliquots comprising crude oil were chosen that were characterized as "non-fouling" (Group 1) according to the criteria described above, and approximately 30 samples were chosen that were characterized as "non-fouling" (Group 2). The samples were first analyzed by NIR to obtain spectral data comprising more than 1300 discrete digitized data points in the range from 4000 to 6000 cm'. Measurements were carried out on an ABB Bomem FT-NIR spectrometer equipped with a deuterated triglycine sulfate (DTGS) detector. Samples were scanned in a fixed 0.5 mm cell with sapphire windows at a temperature of 90° F. (32.2° C.). The spectral resolution was 4 cm' and the number of sample scans and background scans was 32, respectively.

The Group 1 and Group 2 samples (described above) were also each analyzed by $^1$H nuclear magnetic resonance spectroscopy (NMR) to obtain NMR spectral data. A representative $^1$H NMR spectrum of a sample comprising crude oil is shown in FIG. 10, and methods for obtaining such spectral data are both described herein, and conventional in nature. They will therefore not be described in further detail here.

The digitized spectral data obtained by both NIR and NMR was then transformed by wavelet packet transform according to wavelet theory to produce wavelet coefficients data. Each spectrum comprising near-infrared spectral data was decomposed according to wavelet theory using a mother wavelet from the Symlet family of mother wavelets. Decomposition comprised passing the spectral data through two scaling filters: a high pass filter and a low pass filter. As mentioned previously, FIG. 11 demonstrates how the high-pass scaling filter allowed only the high-frequency component of the original spectral data to be converted to an "detail coefficient data set", while the low-pass scaling filter allowed only the low-frequency component of the original spectral data to be converted to an "approximation coefficient data set". Commercially available computer software (for example, but not limited to MATLAB®) may be employed to assist in this transformation but is not required in order to practice the inventive process as described herein.

The process of signal decomposition was continued with different scales of the wavelet filter pair in a step-by-step fashion to separate the noisy components from the signal until the appropriate level of signal decomposition was achieved. Applying the Symlet6 mother wavelet, it was determined that the third level of decomposition or greater allowed discrimination of signal from noise. In certain embodiments, the fourth level of decomposition or greater allowed discrimination of signal from noise. A distinct decrease in ability to discriminate signal from noise occurred when non-Symlet mother wavelets were utilized.

Figure 17:
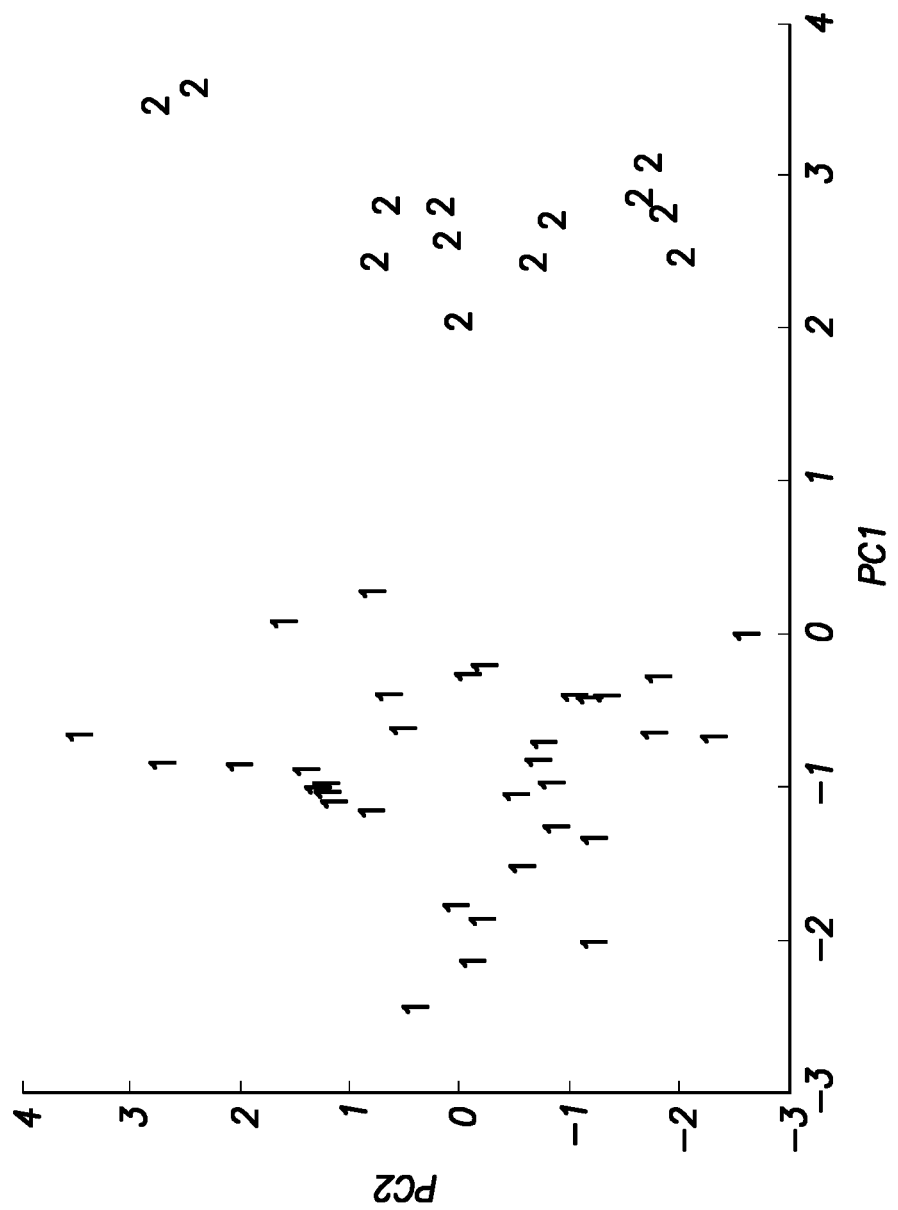
FIG. 17 is a plot of wavelet coefficient data for each of two principle components in crude oil samples that were recognized by pattern recognition genetic algorithm.

The decomposed wavelet coefficient data for each of the 63 crude oil samples were used to train a pattern-recognition genetic algorithm to recognize potential spectral features that might allow the algorithm to distinguish between samples characterized as "fouling" and samples characterized as "non-fouling". Training a pattern-recognition genetic algorithm comprised presenting an untrained genetic algorithm (designed for pattern recognition) with the training wavelet coefficients data obtained from the multiple aliquots representing the first group and the second group, respectively. As the genetic algorithm examined the data and identified potential features in the wavelets coefficients data that could assist in differentiating between the two classes, certain identified potential features were eliminated by manual curation to eliminate identified potential features with the highest probability of being a false positive (i.e., derived from an region of the data that is characterized by a low signal to noise ratio). The process of manual curation can also be thought of as a "search pre-filtering" that pre-screens data that is used by the final trained genetic algorithm to classify samples. Manual curation or pre-filtering served to: 1) decrease the total data to be reviewed by the genetic algorithm when classifying a sample, and 2) assure that potential features that were the result of noise in the data were not utilized by the trained genetic algorithm during classification samples comprising crude oil. The remaining features that were utilized by the trained genetic algorithm for classification typically were associated with spectral features associated with the 2-3 most prevalent classes of chemical components in the sample. One example of classification performed by a trained genetic algorithm is provided in FIG. 17, which depicts wavelet coefficient data for each of two principle components (principle Component 1=PC1; Principle Component 2=PC2) in the training aliquots comprising crude oil, plotted relative to each other. The trained genetic algorithm correctly categorized each aliquot as belonging to either the non-fouling first group (plotted as samples represented by the numeral 1) or the fouling second group (plotted as samples represented by the numeral 2).

Once the pattern recognition genetic algorithm was trained using the various training aliquots the trained genetic algorithm was competent to accurately classify the relative fouling potential of unknown samples comprising crude oil.

Example 3

Figure 18:
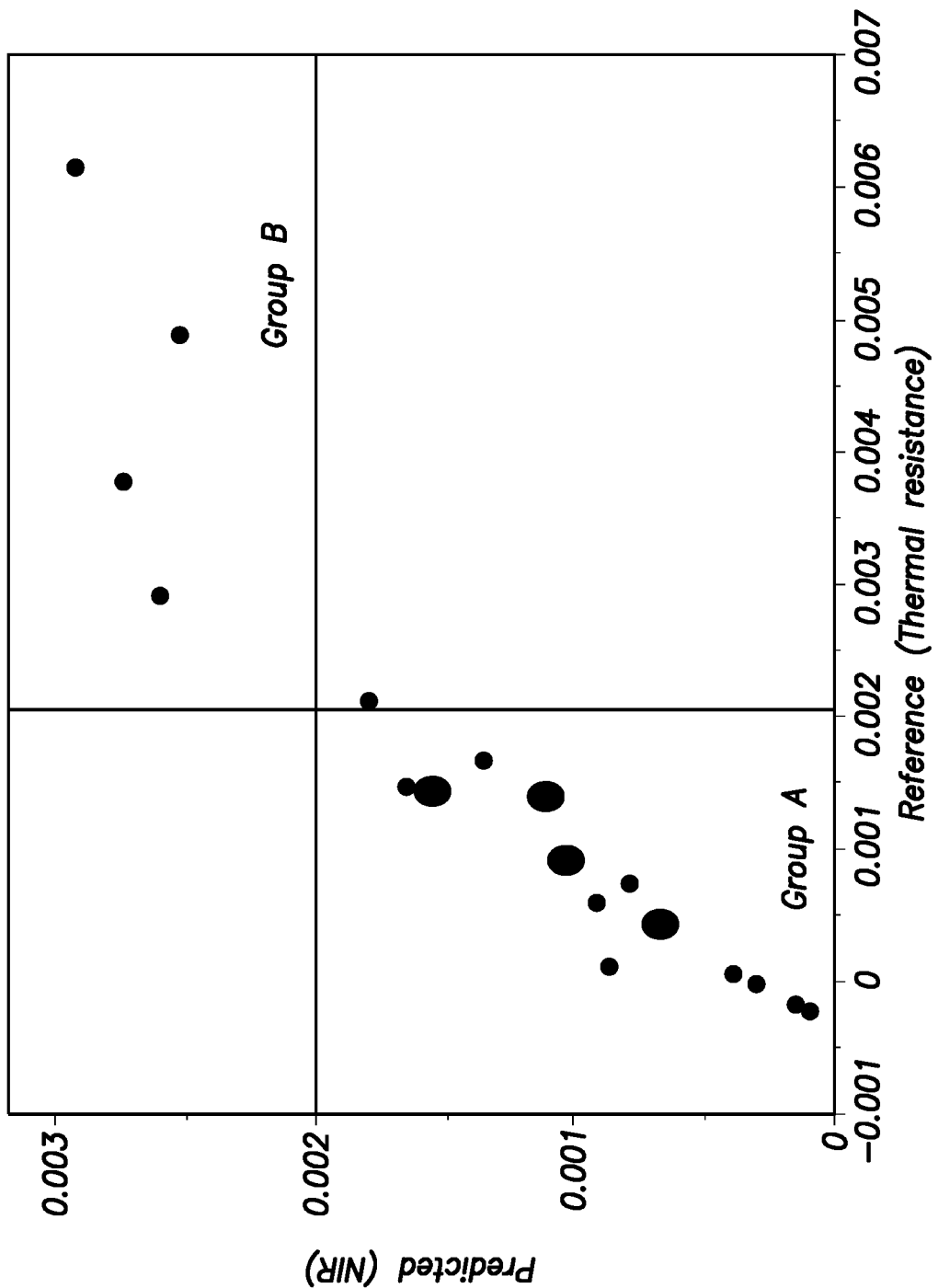
FIG. 18 is a plot representing correlation between the measured fouling thermal resistance (x-axis) for a given training sample versus the fouling thermal resistance predicted by SVM (y-axis).

Certain embodiments utilize support vector machines rather than a genetic algorithm to recognize potential differentiating spectral features in wavelet coefficients data and classify samples comprising crude oil as either fouling or non-fouling. FIG. 18 graphically depicts the strong correlation between measured and predicted fouling potential for a variety of crude oil samples when using SVM to classify samples. The plots predicted fouling thermal resistance for a given sample (using support vector machines) versus the actual fouling thermal resistance of the aliquot measured using the HPLS method described in Example 1. The horizontal and vertical lines through the plotted area represent the threshold fouling thermal resistance that would classify a given sample as either non-fouling (Group A in figure) or fouling (Group B in the figure).

Wavelet coefficients data was first obtained from NIR spectral data (as described herein) for various training aliquots comprising either non-fouling (Group A) or fouling (Group B) crude oil. The wavelets coefficients data was analyzed by SVM to generate a best fit hyperplane through the data (see FIG. 10) that would divide the training aliquots into non-fouling (Group A in the figure) and fouling groups (Group B in the figure), thereby producing a trained SVM. Analyzing of samples comprising crude oil by the trained SVM allowed most samples comprising crude oil to be easily classified according to fouling propensity.

In FIG. 18, each plotted point (small circle) represents the correlation between the measured fouling thermal resistance (x-axis) measured by HPLS (as in Example 1) for a given training sample versus the fouling thermal resistance predicted by SVM (y-axis). The good predictive ability of the SVM to accurately classify the training samples is indicated by the observed strong direct correlation for the training data points (small circles). The trained SVM was then utilized to properly classify four unknown samples comprising crude oil (large ovals), which were all determined to fall within Group A (lower left quadrant of the graph) corresponding to "non-fouling" samples and confirmed the predictive ability of the SVM model. Samples in "Group B" would have been classified as "fouling".

Although the systems and processes described herein have been described in detail, various changes, substitutions, and alterations can be made without departing from the spirit and scope of the invention as delineated by the following claims. Further, the description, abstract and drawings are not intended to limit the scope of the claims to the embodiments disclosed.

In the present description, the term fouling refers to deposit formation, encrustation, scaling, scale formation, slagging, and sludge formation in a petroleum refinery setting, which has an adverse effect on operations. It is the accumulation of unwanted material within a refinery processing unit or on solid surfaces of the unit that is detrimental to function. When it does occur during refinery operations, the major effects include (1) loss of heat transfer as indicated by charge outlet temperature decrease and pressure drop increase, (2) blocked process pipes, (3) under-deposit corrosion and pollution, and (4) localized hot spots in reactors and furnace tubes, all of which lead to production losses and increased maintenance costs. In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A pipeline interchange comprising:
a first product flowing through a first pipeline;
a second product flowing through a second pipeline;
a pipeline interchange connected downstream to both the first pipeline and the second pipeline, wherein the pipeline interchange blends the first product flowing through the first pipeline with the second product flowing through the second pipeline;
a third pipeline connected downstream to the pipeline interchange, wherein the third pipeline flows a blended product created from the blending of the first product and the second product in the pipeline interchange;
an automated analyzer situated downstream of the pipeline interchange capable of physically or chemically analyzing the blended product in the third pipeline and generating blended data; and
a data analyzer capable of interpreting the blended data and communicate adjustments to the flow of both the first product and the second product to achieve desired physical or chemical characteristics in the blended product, and
wherein the automated analyzer is selected from the group consisting of: infrared analyzer, near infrared analyzer, ramen analyzer, acoustic analyzer, UV-visible analyzer, density analyzer, NMR analyzer, viscometer analyzer, terahertz spectroscopy analyzer, conductivity analyzer, pH analyzer, mass spectrometry analyzer, turbidity analyzer, particle size analyzer, electron loss spectroscopy analyzer, fluorescence analyzer, micro- and nano-electromechanical systems analyzers, chromatography analyzer, electrophoresis analyzer, microwave resonance analyzer, cavity-ringdown analyzer, cavity-enhanced analyzer, dielectric spectroscopy, surface plasmon resonance analyzer, quartz crystal microbalance analyzer, biosensing analyzers, time resolved spectrometers, and micro total analytical systems analyzer and combinations thereof, and wherein the analyzing of the data from the automatic analyzer comprises periodically transforming the spectral data to produce transformed spectral data and correlating the transformed spectral data with at least one physical and/or chemical characteristic of the product stream flowing through the upstream pipeline, wherein the correlating indicates a change in the product stream from the first stream to a transmix stream and to a second stream, wherein changes in at least one physical and/or chemical characteristic of the product stream are determined by:
converting the spectral data to discrete digitized data points that are then transformed to produce wavelet coefficients data according to wavelet theory by applying a mother wavelet consisting of a member of the Symlet family of mother wavelets at the third level of decomposition or greater to produce transformed wavelet coefficients data; and
classifying the stream represented by the transformed wavelet coefficients data as either the first stream, a transmix stream or a second stream having distinct chemical characteristics from the first stream by presenting the transformed wavelets coefficients data to a trained genetic algorithm, wherein the trained genetic algorithm performs the classifying by examining identifying data features that collectively identify a particular stream as a member of the first stream, the second stream or a transmix stream.

2. The pipeline interchange of claim 1, wherein the data analyzer utilizes chemometrics to determine the modelling relationship of the blended product to the first product and the second product.

3. The pipeline interchange of claim 2, wherein the modelling relationship is periodically updated from the blended data.

4. The pipeline interchange of claim 1, wherein the automated analyzer physically or chemically analyzes the blended product inside the third pipeline without extracting a sample.

5. The pipeline interchange of claim 1, wherein the automated analyzer physically or chemically analyzes the blended product by extracting a sample from the third pipeline.

6. The pipeline interchange of claim 1, wherein the pipeline interchange controls the flow of the first pipeline and the second pipeline to produce the blended product.

7. The pipeline interchange of claim 1, wherein the flow of the first pipeline is controlled more than 500 meters from the pipeline interchange.

8. The pipeline interchange of claim 1, wherein the flow of the second pipeline is controlled more than 500 meters from the pipeline interchange.

9. A pipeline interchange comprising:
a first product flowing through a first pipeline, wherein first product automated analyzer is situated near the first pipeline to physically or chemically analyze the first product and generate first product data;
a second product flowing through a second pipeline, wherein an optional second product automated analyzer is situated near the second pipeline to physically or chemically analyze the second product and generate second product data;
a pipeline interchange connected downstream to both the first pipeline and the second pipeline, wherein the pipeline interchange blends the first product flowing through the first pipeline with the second product flowing through the second pipeline;
a third pipeline connected downstream to the pipeline interchange, wherein the third pipeline flows a blended product created from the blending of the first product and the second product in the pipeline interchange;
a data analyzer capable of interpreting the blended data; the first product data; and the second product data and communicate adjustments to the flow of both the first product and the second product to achieve desired characteristics in the blended product, and
wherein the automated analyzer is selected from the group consisting of: infrared analyzer, near infrared analyzer, ramen analyzer, acoustic analyzer, UV-visible analyzer, density analyzer, NMR analyzer, viscometer analyzer, terahertz spectroscopy analyzer, conductivity analyzer, pH analyzer, mass spectrometry analyzer, turbidity analyzer, particle size analyzer, electron loss spectroscopy analyzer, fluorescence analyzer, micro- and nano-electromechanical systems analyzers, chromatography analyzer, electrophoresis analyzer, microwave resonance analyzer, cavity-ringdown analyzer, cavity-enhanced analyzer, dielectric spectroscopy, surface plasmon resonance analyzer, quartz crystal microbalance analyzer, biosensing analyzers, time resolved spectrometers, and micro total analytical systems analyzer and combinations thereof, and wherein the analyzing of the data from the automatic analyzer comprises periodically transforming the spectral data to produce transformed spectral data and correlating the transformed spectral data with at least one physical and/or chemical characteristic of the product stream flowing through the upstream pipeline, wherein the correlating indicates a change in the product stream from the first stream to a transmix stream and to a second stream, wherein changes in at least one physical and/or chemical characteristic of the product stream are determined by:

converting the spectral data to discrete digitized data points that are then transformed to produce wavelet coefficients data according to wavelet theory by applying a mother wavelet consisting of a member of the Symlet family of mother wavelets at the third level of decomposition or greater to produce transformed wavelet coefficients data; and classifying the stream represented by the transformed wavelet coefficients data as either the first stream, a transmix stream or a second stream having distinct chemical characteristics from the first stream by presenting the transformed wavelets coefficients data to a trained genetic algorithm, wherein the trained genetic algorithm performs the classifying by examining identifying data features that collectively identify a particular stream as a member of the first stream, the second stream or a transmix stream.

* * * * *